(12) United States Patent
Padgett et al.

(10) Patent No.: US 8,729,236 B2
(45) Date of Patent: May 20, 2014

(54) SELECTION AND CHARACTERIZATION OF NOVEL PLANT-DERIVED RECOMBINANT HUMAN INTERFERONS WITH BROAD SPECTRUM ACTIVITY

(76) Inventors: Hal S. Padgett, Vacaville, CA (US); Fakhrieh S. Vojdani, Davis, CA (US); Andrew A. Vaewhongs, Vacaville, CA (US)

( * ) Notice: Subject to any disclaimer, the term of this patent is extended or adjusted under 35 U.S.C. 154(b) by 0 days.

(21) Appl. No.: 13/478,330

(22) Filed: May 23, 2012

(65) Prior Publication Data

US 2012/0302733 A1 Nov. 29, 2012

Related U.S. Application Data

(60) Provisional application No. 61/489,167, filed on May 23, 2011.

(51) Int. Cl.
*C07K 14/52* (2006.01)

(52) U.S. Cl.
USPC .......................................... 530/351; 424/85.1

(58) Field of Classification Search
None
See application file for complete search history.

(56) References Cited

FOREIGN PATENT DOCUMENTS

EP 0205404 A2 * 6/1986 ............. C12N 15/00

OTHER PUBLICATIONS

Bowie et al. Science, 1990, 247:1306-1310.*
Burgess et al. J. Cell Biol. 111:2129-2138, 1990.*
Lazar et al. Mol. Cell. Biol., 8:1247-1252, 1988.*
Bork. Genome Research, 2000,10:398-400.*

* cited by examiner

*Primary Examiner* — Brian J Gangle
*Assistant Examiner* — Andrea McCollum
(74) *Attorney, Agent, or Firm* — Wayne P. Fitzmaurice

(57) ABSTRACT

Methods to derive novel hybrid type 1 interferons that are broadly active against highly pathogenic viruses of biodefense significance are described. Libraries of hybrid interferon genes were produced using gene shuffling, the proteins were expressed, and screened for activity against viruses of interest. Sequences of several broadly active hybrid interferons are described.

16 Claims, 8 Drawing Sheets

(2 of 8 Drawing Sheet(s) Filed in Color)

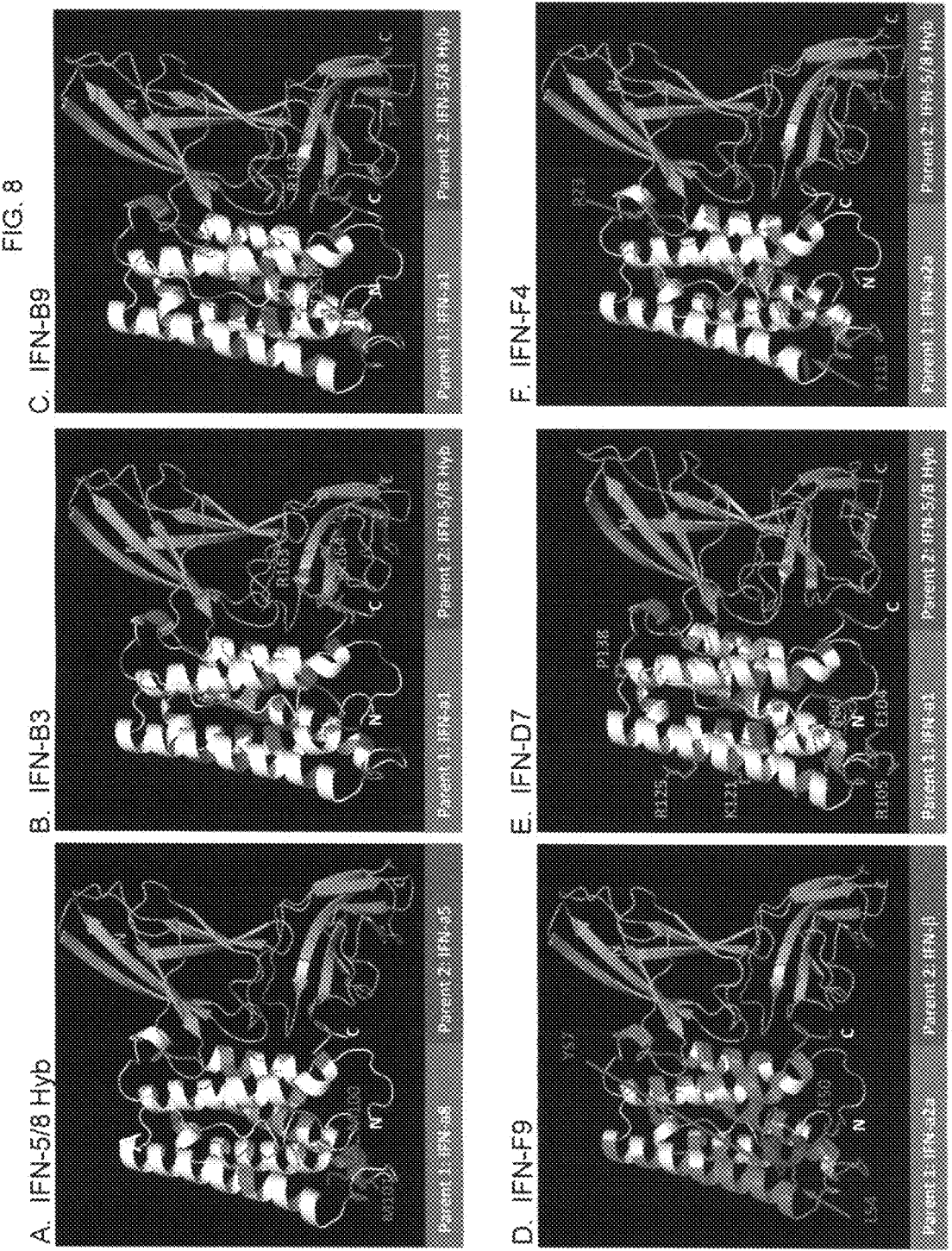

SEQUENCE LISTING

```
<160> NUMBER OF SEQ ID NOS: 31

<210> SEQ ID NO 1
<211> LENGTH: 26
<212> TYPE: PRT
<213> ORGANISM: Nicotiana tabacum

<400> SEQUENCE: 1

Met Gly Lys Met Ala Ser Leu Phe Ala Thr Phe Leu Val Val Leu Val
1               5                   10                  15

Ser Leu Ser Leu Ala Ser Glu Ser Ser Ala
            20                  25

<210> SEQ ID NO 2
<211> LENGTH: 165
<212> TYPE: PRT
<213> ORGANISM: Artificial
<220> FEATURE:
<223> OTHER INFORMATION: IFN variant

<400> SEQUENCE: 2

Cys Asp Leu Pro Gln Thr His Ser Leu Gly Asn Arg Arg Ala Leu Ile
1               5                   10                  15

Leu Leu Ala Gln Met Gly Arg Ile Ser Leu Phe Ser Cys Leu Lys Asp
            20                  25                  30

Arg His Asp Phe Glu Phe Pro Gln Glu Glu Phe Gly His Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Glu Phe Tyr Ile Glu Leu Asp Gln Gln Leu Asn Asp Leu Glu
                85                  90                  95

Ala Cys Met Met Gln Glu Val Gly Val Ile Glu Ser Pro Leu Met Tyr
            100                 105                 110

Glu Asp Ser Ile Leu Ala Val Arg Lys Tyr Phe Gln Arg Ile Thr Leu
        115                 120                 125

Tyr Leu Thr Glu Lys Lys Tyr Ser Ser Cys Ala Trp Glu Val Val Arg
    130                 135                 140
```

Ala Glu Ile Met Arg Ser Leu Ser Phe Ser Thr Asn Leu Gln Lys Arg
145                 150                 155                 160

Leu Arg Arg Lys Glu
            165

<210> SEQ ID NO 3
<211> LENGTH: 167
<212> TYPE: PRT
<213> ORGANISM: Artificial
<220> FEATURE:
<223> OTHER INFORMATION: IFN variant

<400> SEQUENCE: 3

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ala Cys Met Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Arg Arg Lys Glu Leu
            165

<210> SEQ ID NO 4
<211> LENGTH: 165
<212> TYPE: PRT
<213> ORGANISM: Artificial
<220> FEATURE:
<223> OTHER INFORMATION: IFN variant

<400> SEQUENCE: 4

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Glu Phe Pro Glu Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Glu Asp Ser Ser Ala Ala Trp Asp Glu Thr Leu
65                  70                  75                  80

Leu Glu Lys Phe Tyr Ile Glu Leu Asp Gln Gln Leu Asn Asp Leu Glu
                85                  90                  95

Ala Cys Val Ile Gln Gly Val Gly Val Glu Glu Ser Pro Leu Met Tyr
            100                 105                 110

```
Glu Asp Ser Ile Leu Ala Val Arg Lys Tyr Phe Gln Arg Ile Thr Leu
            115                 120                 125
Tyr Leu Thr Glu Lys Lys Tyr Ser Ser Cys Ala Trp Glu Val Val Arg
        130                 135                 140
Ala Glu Ile Met Arg Ser Phe Ser Leu Ser Ile Asn Leu Gln Lys Arg
145                 150                 155                 160
Leu Arg Ser Lys Glu
            165

<210> SEQ ID NO 5
<211> LENGTH: 166
<212> TYPE: PRT
<213> ORGANISM: Artificial
<220> FEATURE:
<223> OTHER INFORMATION: IFN variant

<400> SEQUENCE: 5

Cys Asp Leu Pro Gln Thr His Ser Leu Gly Asn Arg Arg Ala Leu Ile
1               5                   10                  15
Leu Leu Ala Gln Met Arg Arg Ile Ser Pro Phe Ser Cys Leu Lys Asp
            20                  25                  30
Arg His Asp Phe Glu Phe Pro Gln Glu Glu Phe Asp Asp His Gln Phe
        35                  40                  45
Gln Lys Ala Gln Ala Ile Ser Val Leu His Glu Met Ile Gln Gln Thr
    50                  55                  60
Phe Asn Leu Phe Ser Thr Lys Asp Ser Ser Ala Ala Trp Asp Glu Thr
65                  70                  75                  80
Leu Leu Asp Glu Phe Tyr Ile Glu Leu Asp Gln Gln Leu Asn Asp Leu
                85                  90                  95
Glu Ala Cys Met Met Gln Glu Gly Arg Val Ile Glu Ser Pro Leu Met
            100                 105                 110
Tyr Glu Asp Ser Ile Leu Ala Val Arg Lys Tyr Phe Arg Arg Ile Thr
        115                 120                 125
Leu Tyr Leu Thr Glu Lys Lys Tyr Ser Ser Cys Ala Trp Glu Val Val
    130                 135                 140
Arg Ala Glu Ile Met Arg Ser Phe Ser Leu Ser Ile Asn Leu Gln Lys
145                 150                 155                 160
Arg Leu Lys Ser Lys Glu
                165

<210> SEQ ID NO 6
<211> LENGTH: 166
<212> TYPE: PRT
<213> ORGANISM: Artificial
<220> FEATURE:
<223> OTHER INFORMATION: IFN variant

<400> SEQUENCE: 6

Cys Asp Leu Pro Gln Thr His Ser Leu Gly Asn Arg Arg Ala Leu Ile
1               5                   10                  15
Leu Leu Ala Gln Met Arg Arg Ile Ser Pro Phe Ser Cys Leu Lys Asp
            20                  25                  30
Arg His Asp Phe Glu Phe Pro Gln Glu Glu Phe Asp Asp Lys Gln Phe
        35                  40                  45
Gln Lys Ala Gln Ala Ile Ser Val Leu His Glu Met Ile Gln Gln Thr
    50                  55                  60
Phe Asn Leu Phe Ser Thr Lys Asp Ser Ser Ala Ala Leu Asp Glu Thr
65                  70                  75                  80
```

Leu Leu Asp Glu Phe Tyr Ile Glu Leu Asp Gln Gln Leu Asn Asp Leu
                85                  90                  95

Glu Ala Cys Met Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Thr Asn Leu Gln Lys
145                 150                 155                 160

Arg Leu Arg Ser Lys Glu
                165

<210> SEQ ID NO 7
<211> LENGTH: 166
<212> TYPE: PRT
<213> ORGANISM: Artificial
<220> FEATURE:
<223> OTHER INFORMATION: IFN variant

<400> SEQUENCE: 7

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Glu Phe Pro Gln Glu Glu Phe Asp Gly His Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Thr
65                  70                  75                  80

Leu Leu Asp Glu Phe Tyr Ile Glu Leu Asp Gln Gln Leu Asn Asp Leu
                85                  90                  95

Glu Ala Cys Met Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Thr Asn Leu Gln Lys
145                 150                 155                 160

Arg Leu Arg Arg Lys Glu
                165

<210> SEQ ID NO 8
<211> LENGTH: 166
<212> TYPE: PRT
<213> ORGANISM: Artificial
<220> FEATURE:
<223> OTHER INFORMATION: IFN variant

<400> SEQUENCE: 8

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Glu Phe Pro Gln Glu Glu Phe Asp Gly His Gln Phe
        35                  40                  45

```
Gln Lys Ala Gln Ala Ile Ser Val Leu His Glu Met Ile Gln Gln Thr
        50                  55                  60

Phe Asn Leu Phe Ser Thr Glu Asp Ser Ser Ala Ala Leu Asp Glu Thr
 65                  70                  75                  80

Leu Leu Glu Lys Phe Tyr Ile Glu Leu Asp Gln Gln Leu Asn Asp Leu
                85                  90                  95

Glu Ala Cys Val Ile Gln Glu Val Gly Val Glu Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Glu
                165

<210> SEQ ID NO 9
<211> LENGTH: 166
<212> TYPE: PRT
<213> ORGANISM: Artificial
<220> FEATURE:
<223> OTHER INFORMATION: IFN variant

<400> SEQUENCE: 9

Cys Asp Leu Pro Gln Thr His Ser Leu Gly Asn Arg Arg Ala Leu Ile
  1               5                  10                  15

Leu Leu Ala Gln Met Arg Arg Ile Ser Pro Phe Ser Cys Leu Lys Asp
                20                  25                  30

Arg His Asp Phe Glu Phe Pro Gln Glu Glu Phe Asp Asp Lys Gln Phe
            35                  40                  45

Gln Lys Ala Gln Ala Ile Ser Val Leu His Glu Met Ile Gln Gln Thr
        50                  55                  60

Phe Asn Leu Phe Ser Thr Lys Asp Ser Ser Ala Ala Leu Asp Glu Thr
 65                  70                  75                  80

Leu Leu Asp Glu Phe Tyr Ile Glu Leu Asp Gln Gln Leu Asn Asp Leu
                85                  90                  95

Glu Ala Cys Val Met Gln Glu Val Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Lys Ser Lys Glu
                165

<210> SEQ ID NO 10
<211> LENGTH: 166
<212> TYPE: PRT
<213> ORGANISM: Artificial
<220> FEATURE:
<223> OTHER INFORMATION: IFN variant

<400> SEQUENCE: 10

Cys Asp Leu Pro Gln Thr His Ser Leu Gly Asn Arg Arg Ala Leu Ile
  1               5                  10                  15
```

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Gly His Gln Phe
            35                  40                  45

Gln Lys Ala Gln Ala Ile Ser Val Leu His Glu Met Ile Gln Gln Thr
50                  55                  60

Phe Asn Leu Phe Ser Thr Lys Asp Ser Ser Ala Ala Trp Glu Gln Thr
65                  70                  75                  80

Leu Leu Asp Glu Phe Tyr Ile Glu Leu Asp Gln Gln Leu Asn Asp Leu
                85                  90                  95

Glu Ala Cys Met Met Gln Glu Val Gly Val Glu Ser Pro Leu Met
            100                 105                 110

Tyr Glu Asp Ser Ile Leu Ala Val Arg Lys Tyr Phe Gln Arg Ile Thr
            115                 120                 125

Leu Tyr Leu Thr Glu Lys Lys Tyr Ser Ser Cys Ala Trp Glu Val Val
            130                 135                 140

Arg Ala Glu Ile Met Arg Ser Leu Ser Phe Ser Thr Asn Leu Gln Lys
145                 150                 155                 160

Arg Leu Lys Ser Lys Glu
            165

<210> SEQ ID NO 11
<211> LENGTH: 165
<212> TYPE: PRT
<213> ORGANISM: Artificial
<220> FEATURE:
<223> OTHER INFORMATION: IFN variant

<400> SEQUENCE: 11

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Tyr
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
            130                 135                 140

Ala Glu Ile Met Arg Ser Phe Ser Leu Ser Thr Asn Leu Gln Glu Ser
145                 150                 155                 160

Leu Arg Ser Lys Glu
            165

<210> SEQ ID NO 12
<211> LENGTH: 165
<212> TYPE: PRT
<213> ORGANISM: Artificial
<220> FEATURE:
<223> OTHER INFORMATION: IFN variant

```
<400> SEQUENCE: 12

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Glu Asp Ala Ala Leu Thr Ile Tyr Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 13
<211> LENGTH: 166
<212> TYPE: PRT
<213> ORGANISM: Artificial
<220> FEATURE:
<223> OTHER INFORMATION: IFN variant

<400> SEQUENCE: 13

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Glu Phe Pro Gln Glu Glu Phe Asp Gly His Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Asp Glu Thr
65                  70                  75                  80

Leu Leu Glu Lys Phe Tyr Ile Glu Leu Asp Gln Gln Leu Asn Asp Leu
                85                  90                  95

Glu Ala Cys Val Ile Gln Glu Glu Arg Val Gly Glu Ser Pro Leu Met
            100                 105                 110

Tyr Glu Asp Ser Ile Leu Ala Val Arg Lys Tyr Phe Arg Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Glu
                165
```

```
<210> SEQ ID NO 14
<211> LENGTH: 164
<212> TYPE: PRT
<213> ORGANISM: Artificial
<220> FEATURE:
<223> OTHER INFORMATION: IFN variant

<400> SEQUENCE: 14

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ala Cys Met Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Lys Ser

<210> SEQ ID NO 15
<211> LENGTH: 7
<212> TYPE: PRT
<213> ORGANISM: Artificial
<220> FEATURE:
<223> OTHER INFORMATION: INF variant C-terminus

<400> SEQUENCE: 15

Lys Arg Leu Arg Arg Lys Glu
1               5

<210> SEQ ID NO 16
<211> LENGTH: 7
<212> TYPE: PRT
<213> ORGANISM: Artificial
<220> FEATURE:
<223> OTHER INFORMATION: INF variant C-terminus

<400> SEQUENCE: 16

Lys Arg Leu Lys Ser Lys Glu
1               5

<210> SEQ ID NO 17
<211> LENGTH: 7
<212> TYPE: PRT
<213> ORGANISM: Artificial
<220> FEATURE:
<223> OTHER INFORMATION: IFN variant C-terminus

<400> SEQUENCE: 17

Lys Arg Leu Arg Ser Lys Glu
1               5
```

```
<210> SEQ ID NO 18
<211> LENGTH: 7
<212> TYPE: PRT
<213> ORGANISM: Artificial
<220> FEATURE:
<223> OTHER INFORMATION: IFN variant C-terminus

<400> SEQUENCE: 18

Glu Ser Leu Arg Ser Lys Glu
1               5

<210> SEQ ID NO 19
<211> LENGTH: 165
<212> TYPE: PRT
<213> ORGANISM: Homo sapiens

<400> SEQUENCE: 19

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
        50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 20
<211> LENGTH: 166
<212> TYPE: PRT
<213> ORGANISM: Artificial
<220> FEATURE:
<223> OTHER INFORMATION: IFN-alfacon-1

<400> SEQUENCE: 20

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
                20                  25                  30

Arg His Asp Phe Gly Phe Pro Gln Glu Glu Phe Asp Gly Asn Gln Phe
            35                  40                  45

Gln Lys Ala Gln Ala Ile Ser Val Leu His Glu Met Ile Gln Gln Thr
        50                  55                  60

Phe Asn Leu Phe Ser Thr Lys Asp Ser Ser Ala Ala Trp Asp Glu Ser
65                  70                  75                  80

Leu Leu Glu Lys Phe Tyr Thr Glu Leu Tyr Gln Gln Leu Asn Asp Leu
```

```
                    85                  90                  95
Glu Ala Cys Val Ile Gln Glu Val Gly Val Glu Thr Pro Leu Met
            100                 105                 110

Asn Val Asp Ser Ile Leu Ala Val Lys Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Arg Leu Arg Arg Lys Glu
                165

<210> SEQ ID NO 21
<211> LENGTH: 166
<212> TYPE: PRT
<213> ORGANISM: Homo sapiens

<400> SEQUENCE: 21

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Leu Ser Thr Asn Leu Gln Glu
145                 150                 155                 160

Arg Leu Arg Arg Lys Glu
                165

<210> SEQ ID NO 22
<211> LENGTH: 166
<212> TYPE: PRT
<213> ORGANISM: Homo sapiens

<400> SEQUENCE: 22

Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg His Asp Phe Gly Phe Pro Glu Glu Glu Phe Asp Gly His Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80
```

```
Leu Leu Glu Lys Phe Ser Thr Glu Leu Tyr Gln Gln Leu Asn Asp Leu
                85                  90                  95

Glu Ala Cys Val Ile Gln Val Gly Val Glu Glu Thr Pro Leu Met
            100                 105                 110

Asn Glu Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165
```

```
<210> SEQ ID NO 23
<211> LENGTH: 166
<212> TYPE: PRT
<213> ORGANISM: Homo sapiens

<400> SEQUENCE: 23

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
                20                  25                  30

Arg His Asp Phe Gly Phe Pro Gln Glu Glu Phe Asp Gly Asn Gln Phe
            35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Met Met Gln Glu Val Gly Val Glu Asp Thr Pro Leu Met
            100                 105                 110

Asn Val Asp Ser Ile Leu Thr Val Arg Lys Tyr Phe Gln Arg Ile Thr
                115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Ala Asn Leu Gln Glu
145                 150                 155                 160

Arg Leu Arg Arg Lys Glu
                165
```

```
<210> SEQ ID NO 24
<211> LENGTH: 166
<212> TYPE: PRT
<213> ORGANISM: Homo sapiens

<400> SEQUENCE: 24

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
                20                  25                  30

Arg His Asp Phe Glu Phe Pro Gln Glu Glu Phe Asp Lys Gln Phe
            35                  40                  45

Gln Lys Ala Gln Ala Ile Ser Val Leu His Glu Met Ile Gln Gln Thr
    50                  55                  60
```

```
Phe Asn Leu Phe Ser Thr Lys Asp Ser Ser Ala Ala Leu Asp Glu Thr
 65                  70                  75                  80

Leu Leu Asp Glu Phe Tyr Ile Glu Leu Asp Gln Gln Leu Asn Asp Leu
                 85                  90                  95

Glu Val Leu Cys Asp Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Lys Ser Lys Glu
                165

<210> SEQ ID NO 25
<211> LENGTH: 166
<212> TYPE: PRT
<213> ORGANISM: Homo sapiens

<400> SEQUENCE: 25

Cys Asp Leu Pro Gln Thr His Ser Leu Gly Asn Arg Arg Ala Leu Ile
  1               5                  10                  15

Leu Leu Gly Gln Met Gly Arg Ile Ser Pro Phe Ser Cys Leu Lys Asp
                 20                  25                  30

Arg His Asp Phe Arg Ile Pro Gln Glu Glu Phe Asp Gly Asn Gln Phe
             35                  40                  45

Gln Lys Ala Gln Ala Ile Ser Val Leu His Glu Met Ile Gln Gln Thr
 50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                 85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Ile Glu Arg Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 26
<211> LENGTH: 166
<212> TYPE: PRT
<213> ORGANISM: Homo sapiens

<400> SEQUENCE: 26

Cys Asp Leu Pro Gln Thr His Ser Leu Gly Asn Arg Arg Ala Leu Ile
  1               5                  10                  15

Leu Leu Ala Gln Met Gly Arg Ile Ser Pro Phe Ser Cys Leu Lys Asp
                 20                  25                  30

Arg His Asp Phe Gly Phe Pro Gln Glu Glu Phe Asp Gly Asn Gln Phe
             35                  40                  45

Gln Lys Ala Gln Ala Ile Ser Val Leu His Glu Met Ile Gln Gln Thr
```

```
                50                  55                  60
Phe Asn Leu Phe Ser Thr Lys Asp Ser Ser Ala Thr Trp Glu Gln Ser
 65                  70                  75                  80

Leu Leu Glu Lys Phe Ser Thr Glu Leu Asn Gln Gln Leu Asn Asp Met
                 85                  90                  95

Glu Ala Cys Val Ile Gln Glu Val Gly Val Glu Thr Pro Leu Met
                100                 105                 110

Asn Val Asp Ser Ile Leu Ala Val Lys Lys Tyr Phe Gln Arg Ile Thr
                115                 120                 125

Leu Tyr Leu Thr Glu Lys Lys Tyr Ser Pro Cys Ala Trp Glu Val Val
130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 27
<211> LENGTH: 164
<212> TYPE: PRT
<213> ORGANISM: Homo sapiens

<400> SEQUENCE: 27

Tyr Asn Leu Leu Gly Phe Leu Gln Arg Ser Ser Asn Phe Gln Cys Gln
 1               5                  10                  15

Lys Leu Leu Trp Gln Leu Asn Gly Arg Leu Glu Tyr Cys Leu Lys Asp
                 20                  25                  30

Arg Met Asn Phe Asp Ile Pro Glu Glu Ile Lys Gln Leu Gln Gln Phe
                 35                  40                  45

Gln Lys Glu Asp Ala Ala Leu Thr Ile Tyr Glu Met Leu Gln Asn Ile
 50                  55                  60

Phe Ala Ile Phe Arg Gln Asp Ser Ser Ser Thr Gly Trp Asn Glu Thr
 65                  70                  75                  80

Ile Val Glu Asn Leu Leu Ala Asn Val Tyr His Gln Ile Asn His Leu
                 85                  90                  95

Lys Thr Val Leu Glu Glu Lys Leu Glu Lys Glu Asp Phe Thr Arg Gly
                100                 105                 110

Lys Leu Met Ser Ser Leu His Leu Lys Arg Tyr Tyr Gly Arg Ile Leu
                115                 120                 125

His Tyr Leu Lys Ala Lys Glu Tyr Ser His Cys Ala Trp Thr Ile Val
130                 135                 140

Arg Val Glu Ile Leu Arg Asn Phe Tyr Phe Ile Asn Arg Leu Thr Gly
145                 150                 155                 160

Tyr Leu Arg Asn

<210> SEQ ID NO 28
<211> LENGTH: 185
<212> TYPE: PRT
<213> ORGANISM: Homo sapiens

<400> SEQUENCE: 28

Leu Lys Leu Ile Ile Phe Gln Gln Arg Gln Val Asn Gln Glu Ser Leu
 1               5                  10                  15

Lys Leu Leu Asn Lys Leu Gln Thr Leu Ser Ile Gln Gln Cys Leu Pro
                 20                  25                  30

His Arg Lys Asn Phe Leu Leu Pro Gln Lys Ser Leu Ser Pro Gln Gln
                 35                  40                  45
```

```
Tyr Gln Lys Gly His Thr Leu Ala Ile Leu His Glu Met Leu Gln Gln
         50                  55                  60

Ile Phe Ser Leu Phe Arg Ala Asn Ile Ser Leu Asp Gly Trp Glu Glu
 65                  70                  75                  80

Asn His Thr Glu Lys Phe Leu Ile Gln Leu His Gln Gln Leu Glu Tyr
                 85                  90                  95

Leu Glu Ala Leu Met Gly Leu Glu Ala Glu Lys Leu Ser Gly Thr Leu
            100                 105                 110

Gly Ser Asp Asn Leu Arg Leu Gln Val Lys Met Tyr Phe Arg Arg Ile
            115                 120                 125

His Asp Tyr Leu Glu Asn Gln Asp Tyr Ser Thr Cys Ala Trp Ala Ile
130                 135                 140

Val Gln Val Glu Ile Ser Arg Cys Leu Phe Phe Val Phe Ser Leu Thr
145                 150                 155                 160

Glu Lys Leu Ser Lys Gln Gly Arg Pro Leu Asn Asp Met Lys Gln Glu
                165                 170                 175

Leu Thr Thr Glu Phe Arg Ser Pro Arg
            180                 185

<210> SEQ ID NO 29
<211> LENGTH: 180
<212> TYPE: PRT
<213> ORGANISM: Homo sapiens

<400> SEQUENCE: 29

Leu Asp Cys Asn Leu Leu Asn Val His Leu Arg Arg Val Thr Trp Gln
 1               5                  10                  15

Asn Leu Arg His Leu Ser Ser Met Ser Asn Ser Phe Pro Val Glu Cys
                 20                  25                  30

Leu Arg Glu Asn Ile Ala Phe Glu Leu Pro Gln Glu Phe Leu Gln Tyr
             35                  40                  45

Thr Gln Pro Met Lys Arg Asp Ile Lys Lys Ala Phe Tyr Glu Met Ser
         50                  55                  60

Leu Gln Ala Phe Asn Ile Phe Ser Gln His Thr Phe Lys Tyr Trp Lys
 65                  70                  75                  80

Glu Arg His Leu Lys Gln Ile Gln Ile Gly Leu Asp Gln Gln Ala Glu
                 85                  90                  95

Tyr Leu Asn Gln Cys Leu Glu Glu Asp Glu Asn Glu Asn Glu Asp Met
            100                 105                 110

Lys Glu Met Lys Glu Asn Glu Met Lys Pro Ser Glu Ala Arg Val Pro
            115                 120                 125

Gln Leu Ser Ser Leu Glu Leu Arg Arg Tyr Phe His Arg Ile Asp Asn
130                 135                 140

Phe Leu Lys Glu Lys Lys Tyr Ser Asp Cys Ala Trp Glu Ile Val Arg
145                 150                 155                 160

Val Glu Ile Arg Arg Cys Leu Tyr Tyr Phe Tyr Lys Phe Thr Ala Leu
                165                 170                 175

Phe Arg Arg Lys
            180

<210> SEQ ID NO 30
<211> LENGTH: 174
<212> TYPE: PRT
<213> ORGANISM: Homo sapiens

<400> SEQUENCE: 30
```

-continued

```
Leu Gly Cys Asp Leu Pro Gln Asn His Gly Leu Leu Ser Arg Asn Thr
1               5                   10                  15

Leu Val Leu Leu His Gln Met Arg Arg Ile Ser Pro Phe Leu Cys Leu
            20                  25                  30

Lys Asp Arg Arg Asp Phe Arg Phe Pro Gln Glu Met Val Lys Gly Ser
        35                  40                  45

Gln Leu Gln Lys Ala His Val Met Ser Val Leu His Glu Met Leu Gln
    50                  55                  60

Gln Ile Phe Ser Leu Phe His Thr Glu Arg Ser Ser Ala Ala Trp Asn
65                  70                  75                  80

Met Thr Leu Leu Asp Gln Leu His Thr Gly Leu His Gln Gln Leu Gln
                85                  90                  95

His Leu Glu Thr Cys Leu Leu Gln Val Val Gly Glu Gly Glu Ser Ala
            100                 105                 110

Gly Ala Ile Ser Ser Pro Ala Leu Thr Leu Arg Arg Tyr Phe Gln Gly
            115                 120                 125

Ile Arg Val Tyr Leu Lys Glu Lys Lys Tyr Ser Asp Cys Ala Trp Glu
            130                 135                 140

Val Val Arg Met Glu Ile Met Lys Ser Leu Phe Leu Ser Thr Asn Met
145                 150                 155                 160

Gln Glu Arg Leu Arg Ser Lys Asp Arg Asp Leu Gly Ser Ser
                165                 170
```

<210> SEQ ID NO 31
<211> LENGTH: 4
<212> TYPE: PRT
<213> ORGANISM: Artificial
<220> FEATURE:
<223> OTHER INFORMATION: ER retention signal

<400> SEQUENCE: 31

```
Lys Asp Glu Leu
1
```

US 8,729,236 B2

SELECTION AND CHARACTERIZATION OF NOVEL PLANT-DERIVED RECOMBINANT HUMAN INTERFERONS WITH BROAD SPECTRUM ACTIVITY

CROSS-REFERENCE TO RELATED APPLICATIONS

This application claims priority from U.S. Provisional Application No. 61/489,167, filed May 23, 2011. The prior application is hereby incorporated by reference in its entirety.

STATEMENT REGARDING FEDERALLY SPONSORED RESEARCH OR DEVELOPMENT

This work was partially sponsored by Department of the Army contract number W81XWH-05-2-0009.

BACKGROUND OF THE INVENTION

The induction of interferon (IFN) plays a critical role in the antiviral innate immune response. IFNs are classified into type I and type II subgroups according to sequence homologies and receptor specificities. The type I IFNs, which have especially strong antiviral activities and bind to the type I IFN receptor (IFNAR), include IFN-α, IFN-β, IFN-κ, IFN-δ, IFN-ε, IFN-τ, IFN-ω, and IFN-ζ. The best studied of the type I IFNs are IFN-α and IFN-β. These IFNs are produced in response to the sensing of pathogen-associated molecular patterns (PAMPs), such as viral double-stranded RNA, by pattern recognition receptors. IFNs are secreted from the infected cells and bind to IFNAR on nearby cells to initiate signaling cascades that enhance cellular resistance to viral infection [extensively reviewed in (Samuel, 2001)]. IFN-α therapy has been successful in treating viral infections in people, most notably for hepatitis C with the current standard of care for chronic hepatitis C being a combination of IFN-α and the antiviral drug ribavirin (Fried et al., 2002). Recent advances in IFN-α therapy for such viral infections include the addition of a branched 40 kDa polyethylene glycol molecule (pegylation) to synthetic IFN-α, which enhances the effective half-life of the IFN when compared to its native form. Significant improvement was also obtained with a 166 amino acid synthetic, highly potent IFN-α (IFN-alfacon-1), which was derived by comparing predicted amino acid sequences of several natural IFN-α subtypes and assigning the most frequently observed amino acid in each corresponding position resulting in a consensus sequence. Both types of synthetic IFN are now manufactured using bacterial expression methods.

Although not tested in humans, IFN treatment against viruses considered potential bioterrorism or biowarfare threats such as Venezuelan equine encephalitis virus (VEEV) (Lukaszewski and Brooks, 2000), Rift Valley fever virus (RVFV) (Morrill et al., 1989), and Ebola virus (EBOV) (Bray, 2001; Jahrling et al., 1999) has shown efficacy in animal studies. To counteract the potent antiviral effects of IFN these viruses, as well as most or all other viruses, have developed mechanisms to antagonize multiple steps leading to IFN induction or signaling. For example, the VP35 protein of EBOV antagonizes the IFN response by disrupting signaling from the IFN promoter as well as by blocking the phosphorylation and activation of PKR (protein kinase R) (Basler et al., 2000; Feng et al., 2007; Harcourt et al., 1999). In addition, EBOV VP24 counteracts IFN signaling by binding to karyopherin-α nuclear localization signal receptors, thus preventing nuclear localization of the transcription factor STAT1 (signal transducer and activator of transcription 1) (Mateo et al.). For RVFV, a nonstructural protein, NSs, was found to both suppress the transcription of host mRNAs, including IFN mRNAs, and to induce post-transcriptional downregulation of PKR. (Billecocq et al., 2004; Bouloy et al., 2001; Habjan et al., 2009; Ikegami et al., 2009). For VEEV, disruption of tyrosine phosphorylation and nuclear translocation of STAT1 and STAT2 in response to IFN signaling was shown to correlate with expression of nonstructural, but not structural proteins (Simmons et al., 2009; Yin et al., 2009).

Currently, the treatment options for infection with potential biowarfare/bioterrorism viruses are extremely limited. IFNs, especially those that could overcome viral IFN antagonism mechanisms, could provide a prophylactic or therapeutic countermeasure for infection, perhaps in combination with novel antiviral drugs. Attempts to generate enhanced IFN include not only consensus sequence genes, but also genes derived through technologies that randomly blend related genes (gene shuffling) to create unique hybrid expression products with altered biological activities. In studies by others, gene shuffling was used to blend human IFN-α genes to create proteins with enhanced cross-species antiviral activity (Chang et al., 1999). One blended IFN-α was reported to have a 285,000-fold increase in activity compared to human IFN-α2a and a 185-fold increase over human IFN-α1 against encephalomyocarditis virus (EMCV) infection in a cytopathic effect reduction assay with mouse L929 cells (Chang et al., 1999). In another study, gene shuffling was used to derive IFN-α proteins that exhibited superior antiviral potency as well as reduced antiproliferative activity relative to IFN-alfacon-1 (Brideau-Andersen et al., 2007).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The N-terminal extension secretory signal peptide and the C-terminal 6x-His tag-KDEL sequence (KDEL is SEQ ID NO: 31) that was present on each of the hybrid IFNs are not shown in this alignment.

Figure 5:
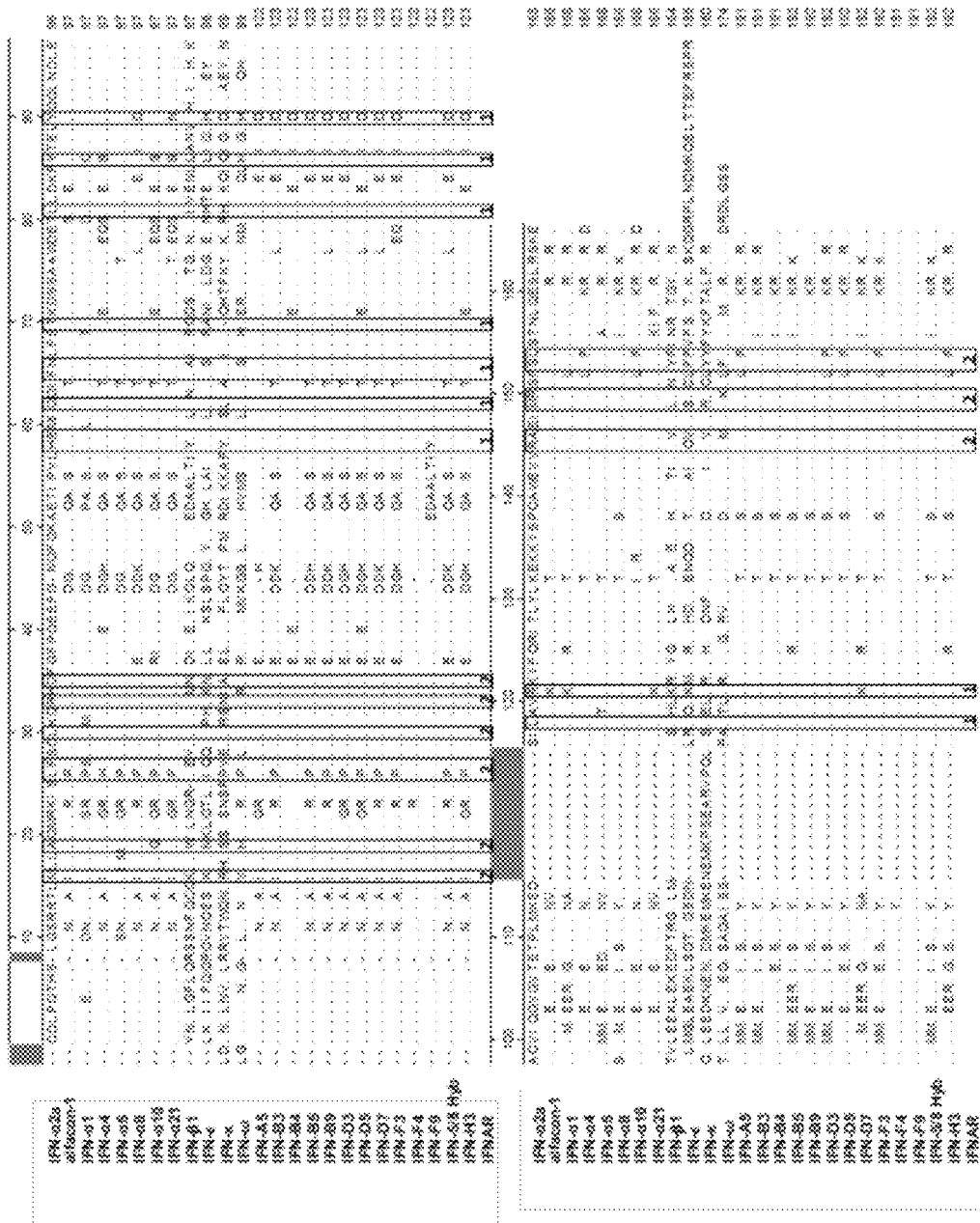
FIG. 5. Sequence comparison of the final set of 13 hybrid IFNs to the type 1 IFN parents and to alfacon-1. Gene sequences were determined for each of the hybrid IFN and derived amino acid sequences were aligned using the Clustal W method of MegAlign™ (DNASTAR Lasergene®) (sequence analysis software). Numbering is according to that of alphacon-1. Amino acids identical to IFN-α2a are hidden. Residues known to be important for receptor binding to IFNAR-1 or IFNAR-2 are indicated by 1 or 2 respectively beneath the boxed amino acids.
Figure 6:
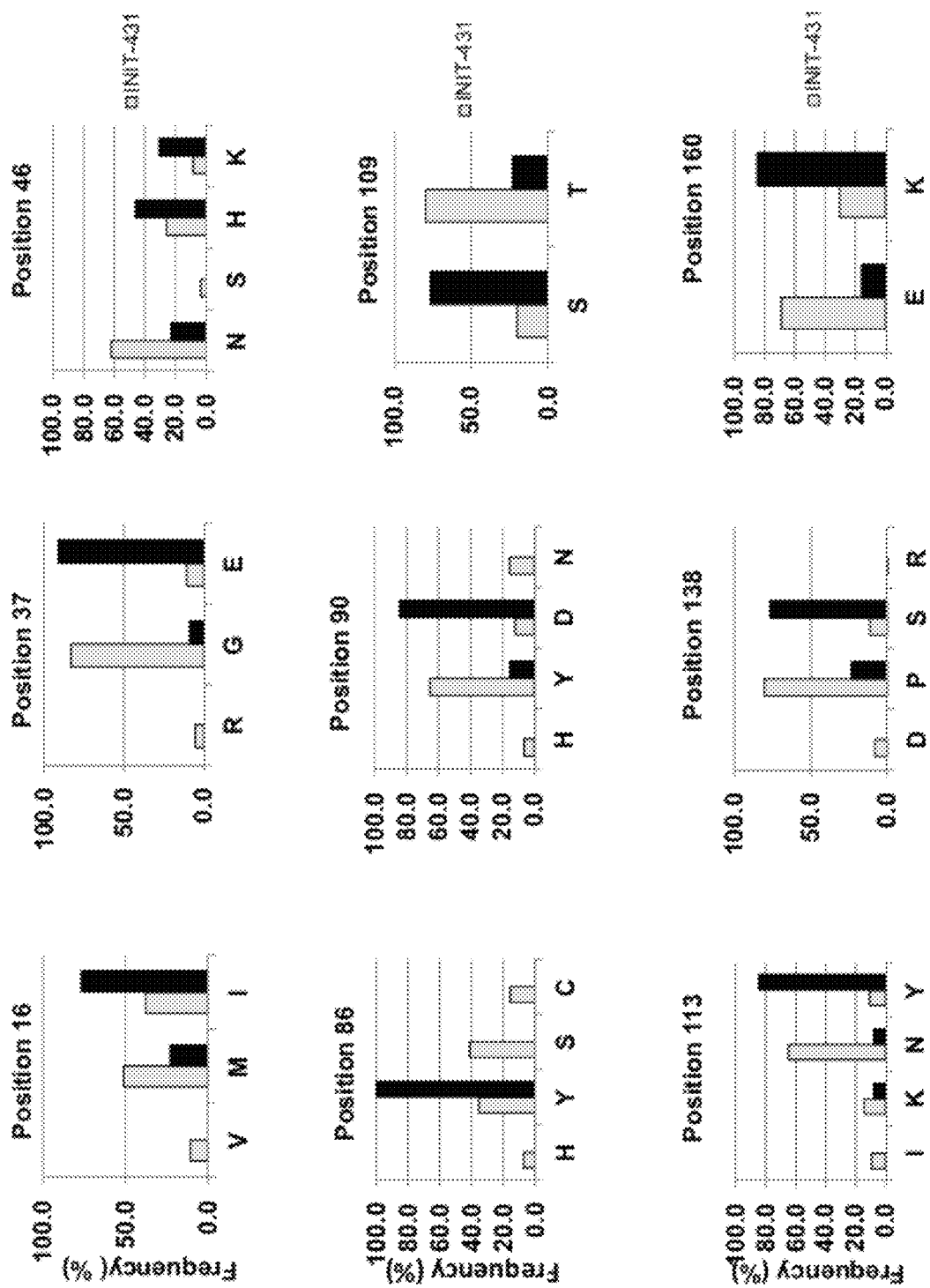

FIG. 6. Amino acid preference at selected positions among the final 13 hybrid IFNs. The derived amino acid sequences from an initial pool of 431 hybridized IFN representative of those resulting from early rounds of GRAMMR were compared to those of the final set of 13 hybrid IFNs. The amino acid frequency (%) is shown at selected positions within the IFN protein. Position numbers correspond to those in FIG. 5.

Figure 7:
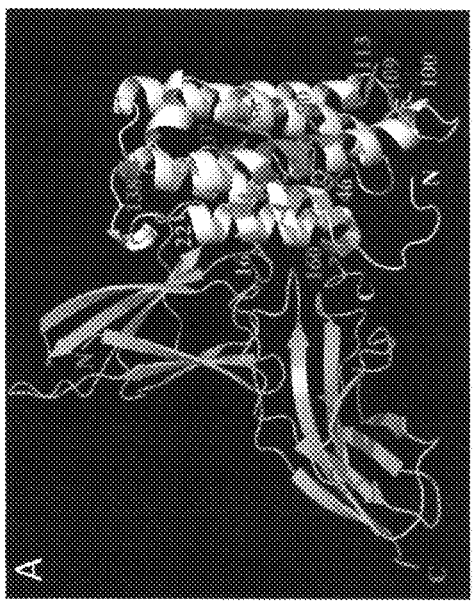
Figure 7:
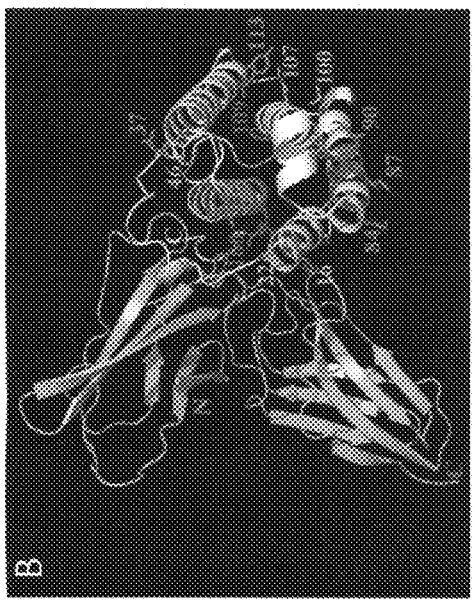
Figure 7:
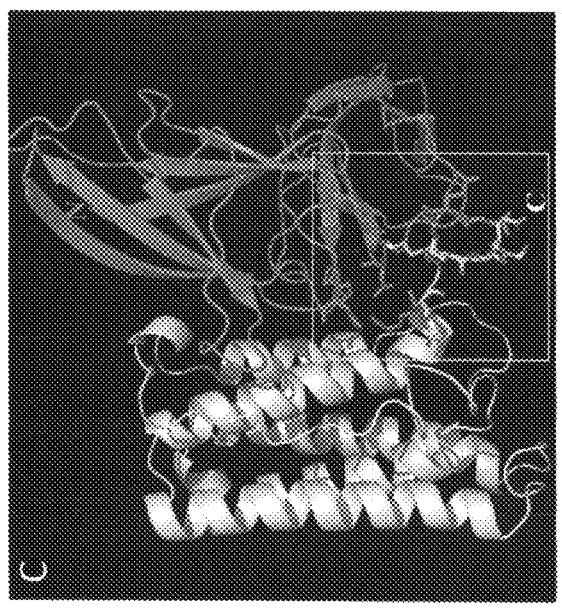
Figure 7:
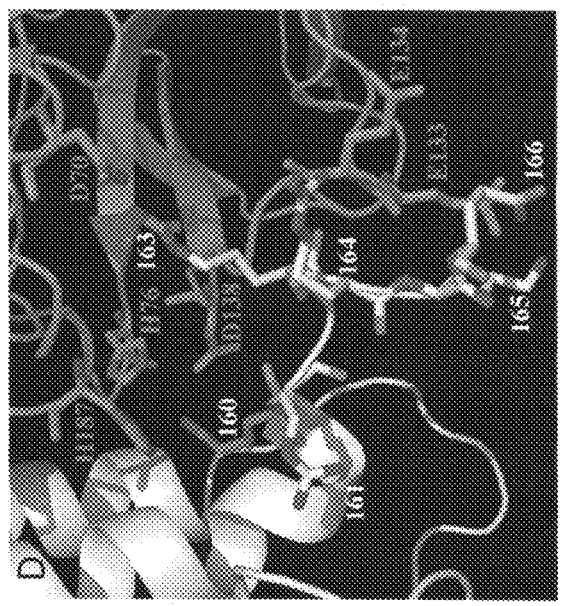

FIG. 7. Structural analysis of shuffled IFNs bound to IFNAR-2. Ribbon diagrams are shown for a complex between IFNAR-2 (green) and a representative shuffled IFN (white). Two different views are shown in panels A and B with selected, high-frequency amino acid changes shown in red (>50% change in frequency) and orange (30-50% change in frequency). Selected amino acids are shown using a "stick" representation to show the predicted direction of the side chains. Shuffled IFN-H3 (green) is shown bound to IFNAR-2 (white) in panel C with the boxed region enlarged in panel D. The boxed and enlarged region highlights the expected residue-residue interactions involving the C-terminal tail (positions 160-166) of the IFN molecule with the receptor. The salt-bridge pairs were inferred by assuming a binding mode equivalent to that observed in the complex between IFN-α2a and IFNAR-2 (PDB code: 2KZ1). A preference for highly-positively charged IFN tails is observed in the final set of shuffled IFN with high potency (FINAL-13). Furthermore, the analysis detects a strong preference for K over E at position 160 in a 4:1 ratio approximately, despite the fact that IFN molecules containing E at position 160 represented roughly ⅔ of the initial pool of shuffled sequences produced (see FIG. 6).

FIG. 8. Structural modeling of selected shuffled IFNs bound to IFNAR-2. Selected shuffled IFNs (A-F) are shown in white bound to IFNAR-2, shown in orange. The indicated parent in the shuffling process is shown in green or blue. Residues considered relevant for determining the molecule potency are shown using a "stick" representation to show predicted side chain orientation.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

In order to derive novel hybrid type 1 IFNs that are broadly active against highly pathogenic viruses of biodefense significance, libraries of hybrid IFN genes were produced using a method of gene shuffling termed Genetic Reassortment by MisMatch Resolution (GRAMMR™), which combines a mismatch endonuclease with a proofreading polymerase and ligase to resolve mismatches in DNA heteroduplexes that are produced by melting and annealing homologous genes. With this process, DNA sequences can be mixed with one another in the context of an entire expression vector to generate hybrid DNAs containing a high frequency of sequence crossovers. Plants were chosen as the expression system for the IFN libraries rather than the more common bacterial expression system used to generate recombinant IFN because of several potential advantages that plants offer for manufacturing biologically active proteins. For example, unlike bacteria, plants have the ability to efficiently produce secreted proteins as well as proteins requiring oxidative crosslinking of cysteines for proper folding. In addition, the system can be cost-effective in that plants can be easy to maintain and large amounts of active recombinant proteins can be readily recovered from extracts of the homogenized plants. Finally, it is possible to individually inoculate hundreds of plants in parallel with the expression vector constructs; thus, it is possible to rapidly produce and evaluate thousands of potential candidate expression products.

Here the results of studies are reported in which the antiviral activities of a plant-derived consensus sequence IFN-α analogous to IFN-alfacon-1 as well as those of hybrid IFNs resulting from several rounds of GRAMMR were measured against EBOV, RVFV, VEEV and monkeypox virus (MPXV). Subtle changes in the IFN genes can result in improved activities against one or even all of the viruses.

Materials and Methods

Reference IFNs and GFP Control

IFN-α2a reference standard (Gxa01-901-535) was obtained from the NIAID Reference Reagent Repository operated by Braton Biotech, Inc. in Gaithersburg Md. Pharmaceutical grade consensus IFN-α (IFN-alfacon-1) reference standard (INFERGEN; Valeant) was obtained by prescription from a pharmacy. In order to generate plant-expressed controls for activity comparisons, His-tagged IFN-α2a (IFN-α2a-His), consensus IFN (IFN-alfacon-His), and His-tagged green fluorescent protein (IFN-αGFP-His) constructs were made for plant-based expression.

Hybrid IFN Gene Library Production

Parental IFN genes used to create the hybrid gene libraries included the IFN-α subtypes IFN-α1, IFN-α2a, IFN-α4, IFN-α5, IFN-α8, IFN-α10 and IFN-α21, as well as the more distantly-related IFN-β, IFN-ε, IFN-κ, and IFN-ω genes that were codon optimized for expression in plants (amino acid sequences are shown in FIG. 5). All encoded the extensin secretory signal peptide from *Nicotiana tabacum* (MGK-MASLFATFLWLVSLSLASESSA, SEQ ID NO: 01) and were C-terminally modified with His(6)-KDEL (KDEL is SEQ ID NO: 31) sequence tags to facilitate purification and increase accumulation in the plant expression host. All of the IFN coding regions were designed to maximize DNA alignment scores with a plant codon optimized IFN-α2a gene, then were synthesized by oligonucleotide assembly and cloned into the pLSBC-DN15 tobamovirus-based plant expression vector (O'Keefe et al., 2009).

Hybrid gene libraries were generated using the GRAMMR™ method (Genetic ReAssortment by MisMatch Resolution) (U.S. Pat. Nos.; 7,056,740, 7,217,514, and 7,833, 759). Briefly, whole-plasmid heteroduplex substrates for the process were generated by linearizing the various pLSBC-DN15-interferon genes with either StuI or SmaI, which cleaved the DNA 4.1 and 5.5 kb upstream of the PacI site, respectively. Linearized plasmids were mixed after purification, heated to 95° C. to dissociate the DNA strands and then cooled to allow strands to anneal to one-another. Aliquots of the different heteroduplex DNA substrates were incubated with reaction cocktails containing RES I, a mismatch endonuclease cloned from *Selaginella lepidophylla* and produced recombinantly (U.S. Pat. Nos.; 7,078,211 and 7,273,739), T4 DNA polymerase, and *E. coli* DNA ligase in various concentrations in *E. coli* ligase reaction buffer containing all four dNTPs. After one hour at 25° C., aliquots from each reaction were used to transform competent DH5-α™ *E. coli* cells (Invitrogen; Carlsbad, Calif.). Resulting colonies were picked and cultured for plasmid DNA production. The nucleotide sequences of most of the resulting plasmid samples were determined to confirm their hybrid nature and intact open reading frames prior to re-array into plasmid sets that were used to generate infectious viral vector RNA transcripts for subsequent plant inoculation and protein production.

Production of IFN in Plants

In 96-well plates, the above described pLSBC-DN15 plasmids containing the hybrid genes in the plant virus-based expression vector were purified and transcribed in vitro using the mMessage mMachine® (in vitro transcription) kit (Ambion, Austin, Tex.). The resulting infectious RNA transcripts were then used to individually inoculate 4-week-old *Nicotiana benthamiana* plants by manual abrasion in the presence of diatomaceous earth. After about 5-7 days post-inoculation, the virus-based expression constructs had each spread throughout the individual host plants and produced their corresponding chimeric proteins. Roughly 2 g of virus-infected plant tissue was harvested from the top of each plant and homogenized in 150 mM Tris-HCl buffer (pH 8.2), 0.5 M NaCl, 15 mM imidazole, 2mM PMSF, and 0.0.15% sodium metabisulfite in 15 ml disposable conical tubes using a glass bead mill constructed from a modified paint shaker. The homogenates were clarified by centrifugation, and 1.5 ml of the supernatant solution was filtered using 96-well Whatman® UNIFILTER® GF/B filter blocks (2 ml well capacity) followed by incubation with 50 μl bed volumes of Ni-conjugated agarose beads (Qiagen, Valencia, Calif.) to bind the His-tagged proteins. Following three centrifugal washes of the beads in the filter block with wash buffer, (50 mM Tri-HCl, pH 8.2, 0.5 M NaCl, 10 mM imidazole, 0.01% Na metabisulfite, 0.2 mM PMSF), the His-tagged IFNs were eluted with 200-240 μl of 0.4 M imidazole-0.1 M Tris-HCl, pH 8.2 containing 0.2 mg/ml BSA. A sample of each purified hybrid IFN was analyzed by SDS-PAGE gel (BioRad Criterion ™, Hercules, Calif.; 16 IFN samples per gel). Proteins were stained with Coomassie® blue and quantified by densitometry and Quantity One® 1-D analysis software (Bio Rad, Hercules, Calif.) using standards of plant-produced, untagged IFN-α2a protein ranging from 0.25 μg to 8 μg. The concentration of each protein was adjusted to 75 ng/ml in phosphate buffered saline (PBS), pH 7.4, containing 1mg/ml BSA using a TECAN automated liquid handler. Following this adjustment, each sample was again quantified by SDS-PAGE and densitometry using a narrower range of IFN standard concentrations to obtain final concentration data used for determination of specific activity values in subsequent bioassays.

For initial screening, 96-well plates were prepared with 16 IFN protein samples each diluted 10-fold across three wells as 30X concentrates of 30,000, 3,000, and 300 pg/ml in RPMI 1640 medium (Gibco®) supplemented with 2 mM L-glutamine, 10 mM HEPES, 1 mM sodium pyruvate, 4.5 g/L glucose, 1.5 g/L sodium bicarbonate, and 10% fetal bovine serum using an automated TECAN liquid handling workstation. IFN-α2a and IFN-alfacon standards, along with medium-only controls, were included in each screening plate. As a control for automation error, duplicate IFN-alfacon samples were included—one prepared in the same manner as test samples using the automated liquid handler and one prepared independently by hand (alfacon-hand). Wells at the outer edges contained medium-only to reduce edge effects. For each 96-well plate of Hybrid IFN samples, 6 such screening plates were prepared, sterilized by passage through 96-well sterile filtration plates (Corning, 0.2um PVDF), and sterile aliquotted with a Robbins Hydra-96® microdispenser (Robbins Scientific, Sunnyvale, Calif.) into sets of replicate 96-well plates. After sealing with sterile aluminum tape seals, the plates were individually vacuum sealed in bags and frozen at −80° C. Prior to use plates were thawed and diluted to working concentrations with sterile medium.

For confirmatory screens on selected hybrid IFNs, each protein was prepared essentially as above. An initial set of 75 proteins was produced and analyzed in duplicate 9-well series of 4-fold dilutions, from approximately 66,000 pg/ml to 1 pg/ml (final), with a no-IFN control in each series and IFN-α2a standards on each plate. The 13 final confirmatory samples were reproduced as described above after re-isolating and re-sequencing the expression constructs to confirm their identity. They were arrayed in 9-well series as described above, in triplicate, along with IFN-α2a controls.

Inhibition of Proliferation Assays

Inhibition of proliferation assays were performed with Daudi cell cultures as described previously (Nederman et al., 1990). Daudi Cells (ATCC: CCL-213) were maintained and assayed in RPMI 1640 medium supplemented with 2 mM L-glutamine, 10 mM HEPES, 1 mM sodium pyruvate, 4.5 g/L glucose, 1.5 g/L sodium bicarbonate, and 10% fetal bovine serum. Daudi cells (4,000/well) from an actively growing culture were incubated in each well of a 96-well clear bottom plate (Costar, N.Y.) in the presence of the IFN samples. After 3 d, cell viability was measured with the Vialight™ Plus cell proliferation kit (Lonza, Walkersville, Md.), and relative light units (RLU) were plotted vs. IFN concentrations as determined from gel densitometry of the normalized protein samples.

Viruses and Cells

The attenuated, luciferase-tagged RVFV rMP12-rluc (Ikegami et al., 2006) virus was kindly provided by Dr. Shinji Makino of the University of Texas Medical Branch at Galveston (Galveston, Tex.). The green-fluorescent protein (GFP)-tagged Zaire ebolavirus, EboZ-eGFP (Towner et al., 2005), was kindly provided by Dr. Jonathan Towner, Centers for Disease Control and Prevention (Atlanta, Ga.). The MPXV-GFP virus was produced as previously described for cowpox (Falkner and Moss, 1988; Goff et al., 2007). Briefly, plasmid pSJH7-EGFP, containing the EGFP gene controlled by the vaccinia virus p7.5 promoter and flanked by homologous recombination sites J4R and J5L (Goff et al., 2007), was transfected into CV-1 cells infected with wild-type MPXV. After 48 h cells were suspended in Dulbecco's Modified Eagle Medium (DMEM), freeze/thawed three times, and sonicated. Virus was serially diluted and was used to infect a monolayer of BS-C-1 cells. Following a 2 h adsorption, a 1% low gelling temperature agarose overlay containing DMEM, 25 μg/ml mycophenolic acid, 250 μg/ml xanthine, and 15 μg/ml hypoxanthine was applied. Cells were incubated for 3 days at 37° C., and a secondary, 1% low gelling agarose overlay containing 0.01% (v/v) neutral red, was applied. Following 2 h incubation at 37° C., plaques were aseptically picked, re-suspended in DMEM as described above, and two additional rounds of plaque purification were completed. Recombinant virus was screened for GFP expression by infecting human hypoxathine phosphoribosyltransferase negative cell line D98OR supplemented with 2 μg/ml 6-thioguanine and screening for GFP fluorescence.

To generate a luciferase-tagged VEEV, a plasmid encoding the non-structural protein 3 (nsP3) gene of VEEV was subjected to transposon insertional mutagenesis with a Mutation Generation System kit (Finnzymes, Espoo, Finland) to produce a clonal library having a 15 base pair insertion site containing a NotI restriction site inserted into random locations within nsP3. A cassette consisting of firefly luciferase flanked by NotI sites was inserted into the NotI insertion mutants present in the starting library. nsP3-luciferase fusions were excised from this secondary library by restriction digestion and cloned into a full-length genomic clone of VEEV, generating a final library that consisted of full length VEEV clones with nsP3-luciferase fusions. The final library was transcribed in vitro, and the resulting RNA was transfected into BHK cells to generate replication-competent VEEV. Supernatant solutions containing replicating viruses were harvested after significant cytopathic effects (CPE) were observed. Two insertion sites, immediately after nucleotides 5341 and 5431 (relative to the genome of the Trinidad donkey strain of VEEV, Genbank accession number L01442) were identified multiple times in independent sequencing events and were chosen for further development. Infectious clones containing luciferase fusions after either nucleotide 5341 or 5431 were constructed, and virus was generated from those clones by reverse genetics as described above. Significant CPE was observed after transfection of in vitro transcribed RNA from these two clones. The supernatant solution was collected and transferred to fresh Vero cells, and luciferase activity was determined 24 hours after transfer of the supernatant solutions (Steady Glo®, Promega, Madison, Wis.). Cells infected with supernatant solutions from both clones had roughly equal luciferase activity. The virus containing the luciferase fusion at nt 5431 was chosen for use in the IFN assays. Cells used for the virus inhibition assays were propagated in either DMEM supplemented with 10% FBS (RVFV and VEEV) or MegaVir™(Hyclone™, Logan, Utah); (EBOV and MPXV).

Virus Inhibition Assays

Vero E6 cells (ATCC CRL-1586, for RVFV and MPXV) or Vero 76 cells (ATCC CRL-87, VEEV and EBOV) were seeded in 96-well luminometer plates. Once cells had reached confluency (approximately 72 h later), IFN diluted from approximately 60,000 pg/ml to 1 pg/ml was added for 24 h. Cells were then infected with predetermined, signal-optimized amounts of virus. Both the luciferase-tagged VEEV and RVFV assays were read 18 h post infection using the Steady-Glo® (VEEV) or Renilla (RVFV) luciferase assay systems (Promega) according to the manufacturer's instructions. Both the GFP-tagged viruses, MPXV and EBOV, were assayed for fluorescence 48 h after infection.

Protein Modeling

The Protein Structure Prediction Pipeline (PPSP) (Lee et al., 2009) was used to generate 3D models for the high-potency set of IFN proteins. The PSPP contains a suite of open-source software that allows for the prediction of protein structures from sequence through the integration of multiple programs including domain boundary detection, sequence homology search, fold recognition, homology modeling, de novo design, and model evaluation. The PSPP uses the program NEST (Petrey et al., 2003) for generating homology models. Two types of input data were used to produce these 3D models: (a) template files corresponding to the experimentally determined structures of (i) IFNα2a (Klaus et al., 1997), and (ii) IFNα2 bound to an IFN α/β receptor (Nudelman et al.) retrieved from the Protein Data Bank (PDB) (Berman et al., 2000); and (b) sets of pair-wise alignments between each of the target IFN sequences and that of the template structures. Models based on different templates were built to assess the variability of unique parts of the structure, particularly those involving regions of the IFN molecules that were expected to be in contact with the receptor. Analysis of the final structures was performed with the help of graphic tools provided with the programs PyMOL (pymol.org) and DS-Modeling (Accelrys).

Statistical Analysis

Data were analyzed using GraphPad Prism® (software) using a nonlinear, variable slope regression analysis. Each hybrid IFN was compared to the control IFN-α-2a-His using the extra sum-of-squares F test to determine if there was a significant difference between the IFN concentration required to decrease viral or Daudi cell replication by 50 ($IC_{50}$) and 90 ($IC_{90}$) percent.

Results

Generation of Hybrid IFN Genes and Expression in Plants

Hybrid IFN-α genes were created by either single or repeated rounds of GRAMMR of plasmids with genes from the IFN-α subtypes. The parental IFN-α gene open reading frames (ORF) used to produce these IFN-α/IFN-α subtype libraries shared between 88% and 97% nucleotide identity (86% to 97% without the secretory leader and C-terminal tag sequences). In a preliminary IFN-α/IFN-α library production and screening study, one hybrid IFN-α was identified that exhibited enhanced activity in antiviral assays along with a marked increase in protein yield in plants. This gene, which was comprised of mostly IFN-α8 with four contiguous amino acids from IFN-α5 (termed IFN-α5/8 hyb, sequence shown in FIG. 5) was included with the set of IFN-α subtype genes to generate subsequent IFN-α/IFN-α gene libraries. In addition to IFN-α/IFN-α libraries, libraries of hybrid IFNs were generated by various pairings of IFN-α genes with IFN-β, IFN-ε, IFN-κ, or IFN-ω genes. The IFN-w gene ORF shared between 81% and 84% nucleotide identity (77% to 79% without the secretory leader and C-terminal tag sequences) with the various IFN-α subtypes, while the with IFN-β, IFN-ε, IFN-κ genes shared between 62% and 72% sequence identity (55% to 63% without the secretory leader and C-terminal tag sequences) with the ORF of the IFN-α genes. Typical single-round recombination frequencies ranged from an average of 9 to 13 crossovers per kB for the IFN-α/IFN-α subtype libraries while the IFN-α genes combined pair-wise with IFN-β, IFN-ε, IFN-κ, or IFN-ω genes contained an average of about 3.5 crossovers per kb among the hybrid products.

Figure 1:
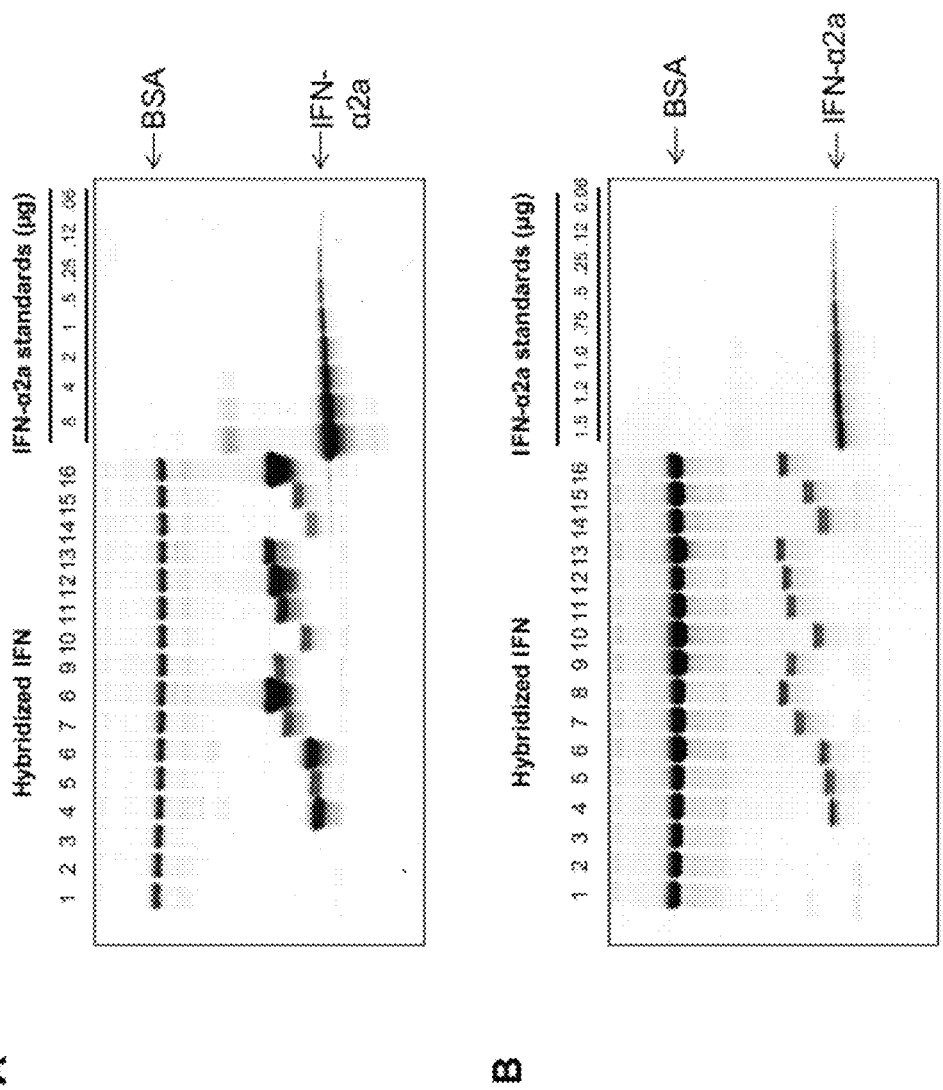
FIG. 1. Comparison of hybrid IFN protein yields from *Nicotiana benthamiana* plant homogenates. His-tagged hybrid IFN proteins were purified from plant homogenates by binding to Ni-conjugated agarose beads. A sample of each purified hybrid IFN was analyzed by SDS-PAGE and staining with Coomassie blue, then quantified by densitometry as compared to standards of plant-produced, untagged IFN-α2a. (A) Relative yields of IFN before normalization. Lanes 1-3 are samples that were rejected due to low yields. (B) Samples were normalized (except for those in lanes 1-3) and quantified using a narrower range of standards for comparison. Top arrow indicates BSA, included in the purification buffer to stabilize the IFN proteins. Bottom arrow indicates IFN-α2a standard.

The resulting hybrid IFN proteins were produced in plants using a transient, virus-based expression system coupled with a 96-well His-tag protein purification process. The concentrations of the purified proteins in elution buffer were measured by SDS-PAGE gel densitometry, which, although laborious, was highly reproducible. Protein levels ranged from undetectable to greater than 5000 ng/μl (e.g., FIG. 1A). To ensure maximal yield of the final gene product, unacceptably low-yielding clones were excluded from subsequent rounds of GRAMMR (e.g., FIG. 1, first 3 lanes). Most of the hybrid IFNs resulting from IFN-α/IFN-αGRAMMR (~1400 in all) produced sufficient amounts of protein for purification and downstream processing; however, only 180 of the ~2000 IFN-α/IFN-β, -ε,-κ hybrid IFN produced enough protein for further studies. To increase the yield and stability of the IFNs, the parental genes had been modified to include codons for the amino acids KDEL (SEQ ID NO: 31) at the C-terminus of each of the proteins, which helps to compartmentalize the protein to the endomembrane system of the plant. A sample set of purified hybrid IFN proteins were analyzed by mass spectrometry (MALDI-TOF) to verify that the proteins were of the expected size for the mature folded forms (not shown). Mass spectrometry, as well as SDS-PAGE analysis, indicated that in most of the purified protein samples, a fraction of the molecules had undergone removal of the C-terminal KDEL (SEQ ID NO: 31) sequence (e.g., FIG. 1, doublet IFN bands), likely by protease activity in the secretory system of the plant cells.

Comparison of Plant- and Bacteria-Derived Control IFNs

Figure 2:
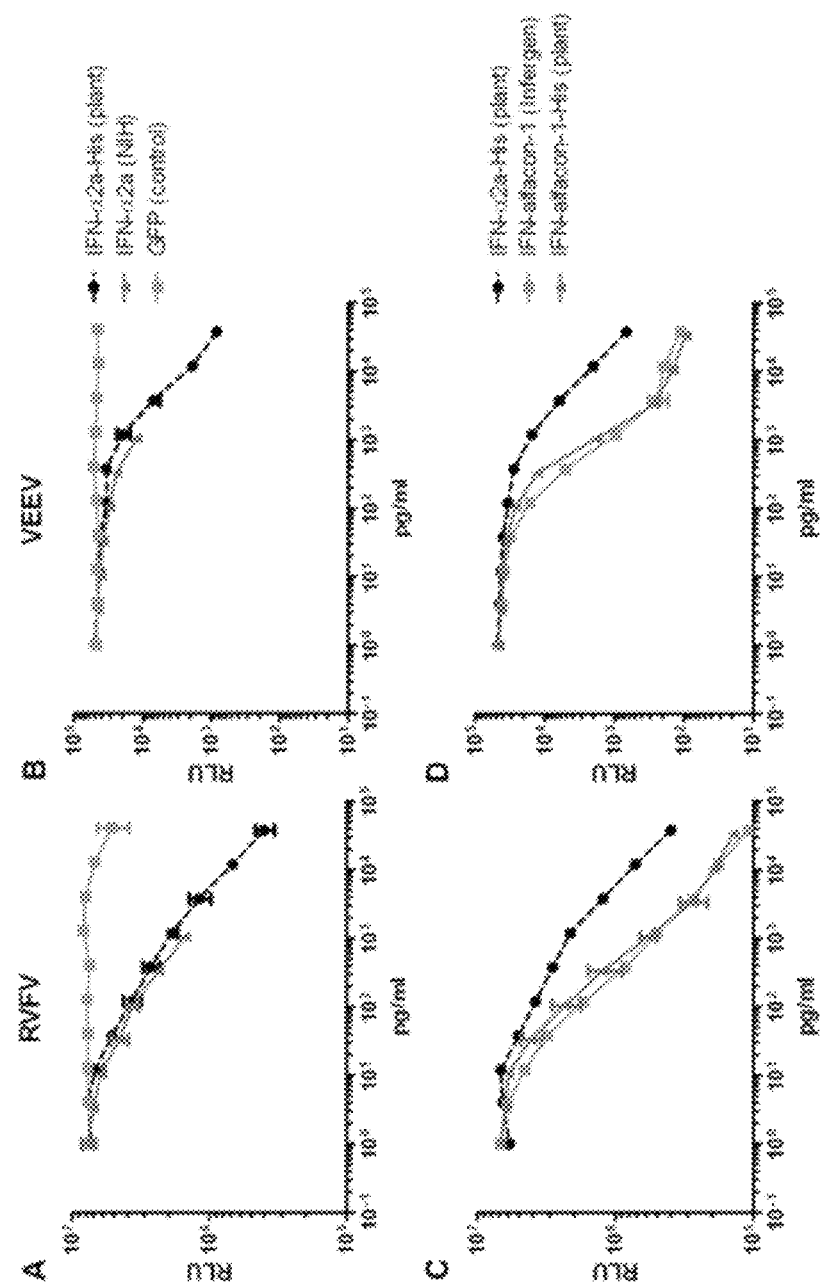
FIG. 2. Antiviral activities of plant derived IFNs. (A and B) Inhibition of the RVFV and VEEV luciferase reporter viruses were compared for IFN-α2a-His (plant) and the NIH standard IFN-α2a (NIH) or (C and D) pharmaceutical-grade IFN-alfacon-1 (Infergen) and the plant-expressed IFN-alfacon-1-His (plant). Cells were incubated with IFN 24 h prior to infection, and relative light units (RLU) were measured after 18 h or 48 h, (A and B, respectively). The GFP control treatment comprised a 6xHis tagged GFP gene, expressed in plants, and was intended to demonstrate that these modifications and plant expression by themselves do not interfere with viral replication. Each concentration was run in duplicate, and error bars indicate standard deviation.

To allow comparison of the instant results to those of others obtained using the NIH standard IFN control, same plate evaluations of the antiviral activities against RVFV and VEEV of the plant-derived IFN-α2a-His and the NIH reference standard IFN-α2a were performed. Assays were conducted on Vero cells, which do not produce type 1 IFN, but have IFN receptors so can respond normally to exogenous IFN (Desmyter et al., 1968; Mosca and Pitha, 1986). IFN concentrations were normalized for samples with sufficient protein for analysis (e.g., FIG. 1B, $4^{th}$-$16^{th}$ lanes), and dilutions were added to cells one day before they were infected with the reporter viruses. The levels of viral replication were measured one day later, and dose-response curves were generated. The results show that the plant- and bacterial-derived IFN-α2a proteins have similar inhibition kinetics with the viruses tested; thus the plant expression and the presence of the His-tag do not appear deleterious to the antiviral effects of the IFN (FIG. 2A, B). In a separate experiment, the activity of the pharmaceutical grade consensus IFN-alfacon-1 (INFERGEN) was compared to the plant-derived IFN-α2a-His or IFN-alfacon-His with RVFV and VEEV. Curves generated with INFERGEN and the plant IFN-alfacon were very similar, although the INFERGEN appeared slightly more potent (FIG. 2C, D). Based on calculated $IC_{50}$ and $IC_{90}$ values (Table 1), both the plant-derived and bacteria-derived IFN-alfacon proteins inhibited RVFV and VEEV better than IFN-α2a-His.

TABLE 1

Comparison of plant expressed and standard IFNs with VEEV and RVFV

| | Rift Valley fever virus | | | | Venezuelan equine encephalitis virus | | | |
|---|---|---|---|---|---|---|---|---|
| | $IC_{50}$ (pg/ml) | P-value vs. IFN-a2a-His (plant) | $IC_{90}$ (pg/ml) | P-value vs. IFN-a2a-His (plant) | $IC_{50}$ (pg/ml) | P-value vs. IFNa2a-His (plant) | $IC_{90}$ (pg/ml) | P-value vs. IFN-a2a-His (plant) |
| IFN-a2a-His (plant) | 215.9 | | 4235 | | 586.2 | | 12022 | |
| IFN-alfacon-1 (Infergen) | 21.26 | <0.0001 | 400.9 | 0.0005 | 76.22 | | 508.5 | |
| IFN-alfacon-1-His (plant) | 51.52 | 0.0009 | 489.9 | 0.0083 | 140.4 | <0.0001 | 1060 | <0.0001 |
| IFN-alfacon-1 (Infergen) vs. IFN-alfacon-1-His (plant) | | <0.0001 | | 0.5216 | | <0.0001 | | 0.0059 |

Down-selection of Hybrid IFNs

Figure 3:
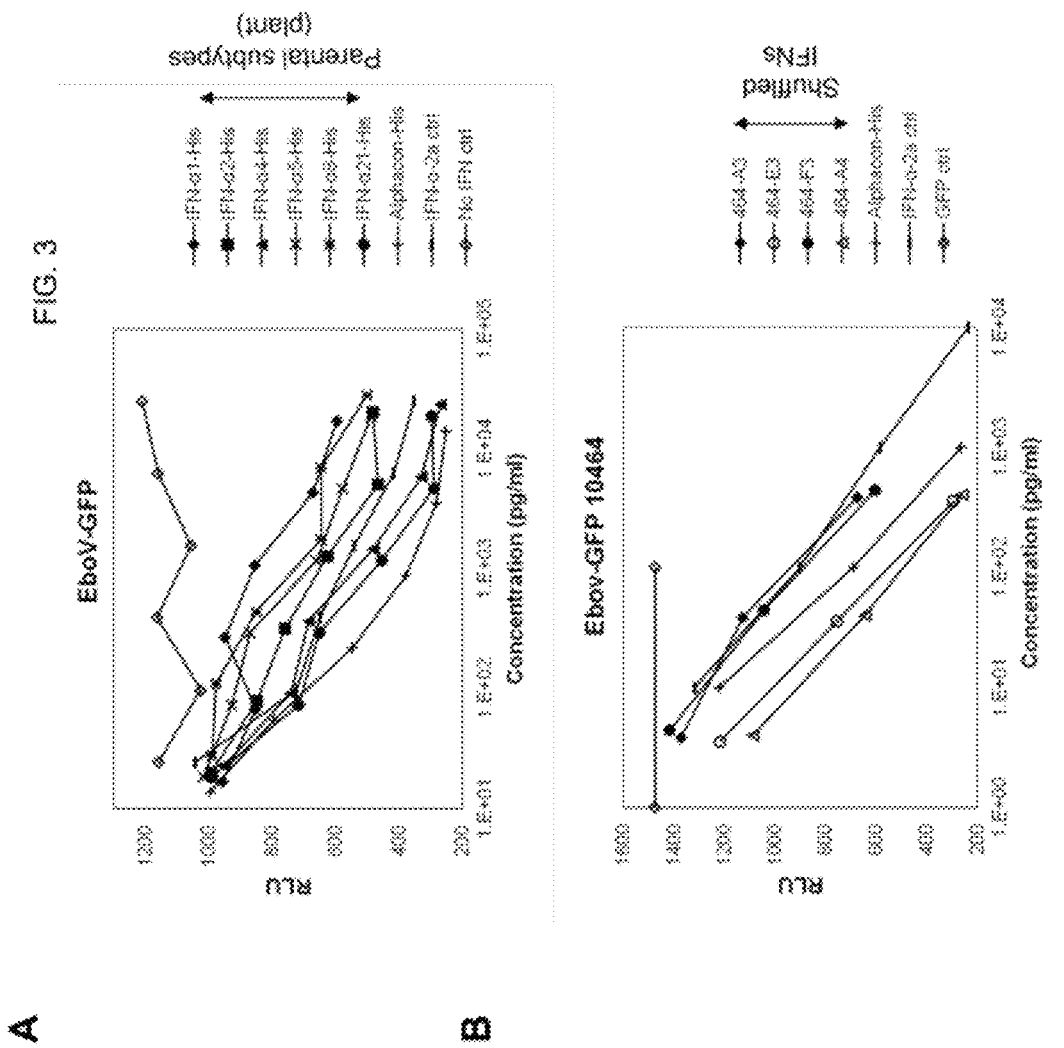
FIG. 3. Antiviral activity against EBOV of hybridized IFNs after three rounds of GRAMMR. Cells were incubated with serial dilutions of IFN for 18 h prior to infection with EboZ-eGFP. Forty-eight hours post-infection, GFP levels were read. Plant-expressed IFN parental subtypes are shown in panel A, and Panel B shows 4 selected shuffled IFNs with plant-expressed IFN-alphacon-1-His.

After one to three rounds of GRAMMR shuffling, hybrid proteins were assessed to identify those with the highest antiviral activities. For this, cells were incubated with serial dilutions of the hybrid IFNs (single well per dilution) or with control IFNs before infection with the reporter viruses. As expected, the plant-derived IFN-alfacon-His showed stronger antiviral activity than any of the parental IFN (e.g., FIG. 3A, shown for EBOV). Most of the IFN-α/IFN-α and IFN-α/IFN-ω hybrid IFNs were active against one or more of the viruses, and a few showed stronger activity than IFN-alfacon-His (e.g., FIG. 3B, Clones E3 and A4 shown with EBOV). In contrast, about one-third of the IFN-α/IFN-β, IFN-α/IFN-ε, or IFN-α/IFN-κ hybrid IFNs showed little or no antiviral activity, indicating that dramatic shifts in protein sequence/structure might not be tolerated. Based on this screening, a set of 75 candidates showing broad spectrum and/or enhanced inhibition as compared to controls were selected for a confirmatory round of screening with each of the four reporter viruses. For this confirmatory screening, additional quantities of the hybrid proteins were produced, and their antiviral activities were tested with each virus in duplicate across a broader range of concentrations (data not shown). Based on the results of this screening, 13 hybrid IFNs were selected for further study. This set included 12 hybrid IFN that had undergone several rounds of GRAMMR, as well as the IFN-5/8 Hyb described in section 3.1 (Table 2).

TABLE 2

Antiviral activity of the shuffled IFNs against RVFV and VEEV

Figure 4:
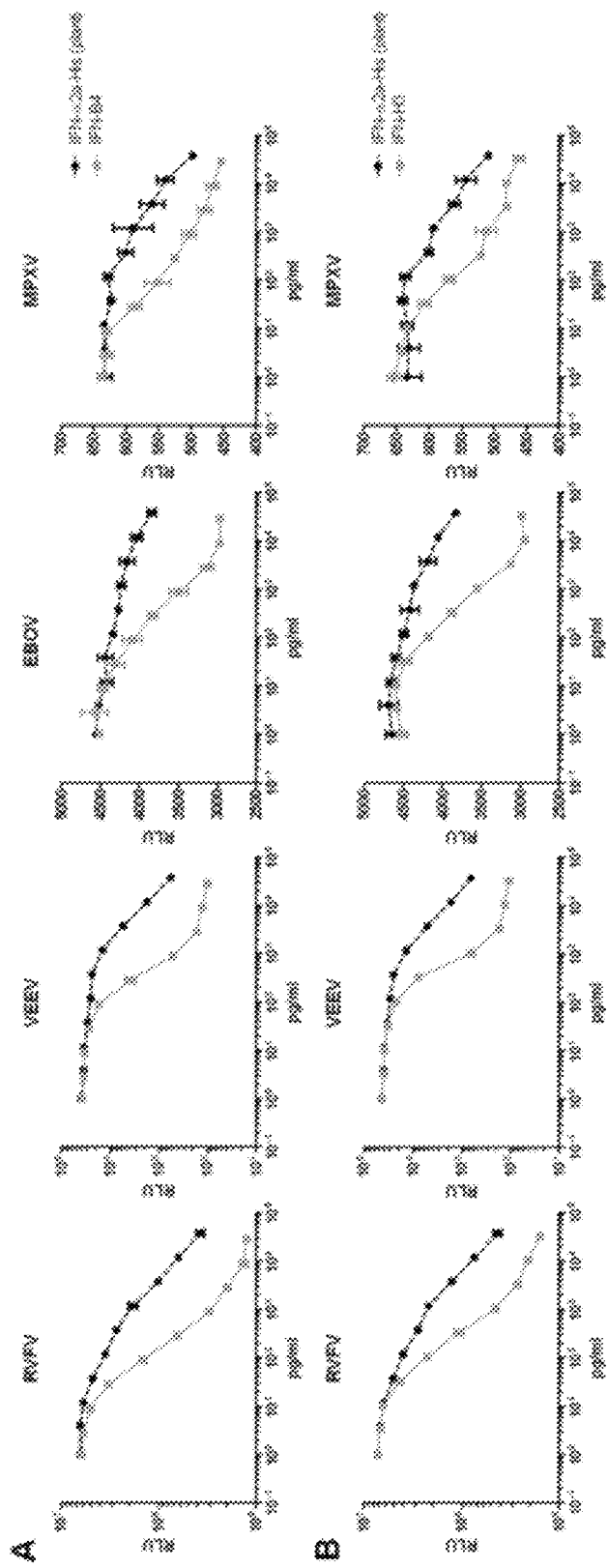
FIG. 4. Inhibitory activities of hybrid IFN against RVFV, VEEV, EBOV and MPXV. Cells were incubated with either a hybrid IFN or IFN-α2a-His for 18 h before infection with reporter viruses. Luciferase activity was measured 24 h post infection for VEEV and RVFV. Both EBOV and MPXV were assayed for GFP fluorescence 48 h post infection and dose response curves were generated for (A) IFN-B4 (A) and (B) IFN-H3

| | Rift Valley fever virus | | | | | | Venezuelan equine encephalitis virus | | | | | |
|---|---|---|---|---|---|---|---|---|---|---|---|---|
| | IC50 (pg/ml) | | | IC90 (pg/ml) | | | IC50 (pg/ml) | | | IC90 (pg/ml) | | |
| IFN | Drug | IFN-a2a-His (plant) | P-value | Drug | IFN-a2a-His (plant) | P-value | Drug | IFN-a2a-His (plant) | P-value | Drug | IFN-a2a-His (plant) | P-value |
| A5 | 19.08 | 132.8 | <0.0001 | 251.5 | 5260 | <0.0001 | 59.42 | 351.9 | 0.0189 | 385.1 | >max | |
| B3 | 18.24 | 105.3 | <0.0001 | 730.9 | 3561 | 0.002 | 91.98 | 541 | <0.0001 | 1053 | 26194 | <0.0001 |
| B4 | 29.04 | 144.7 | <0.0001 | 204.1 | 6060 | <0.0001 | 74.49 | 744.9 | x | 395 | >max | |
| B5 | 30.23 | 136.3 | <0.0001 | 462.3 | 5030 | <0.0001 | 97.26 | 701.2 | x | 696.8 | 33167 | <0.0001 |
| B9 | 41.67 | 105 | 0.003 | 551.3 | 3043 | 0.0065 | 126.2 | 728 | <0.0001 | 1248 | >max | |
| D3 | 65.64 | 138.4 | 0.0063 | 1700 | 6622 | 0.0277 | 177.4 | 735.3 | <0.0001 | 2949 | 18879 | 0.0036 |
| D5 | 43.9 | 153.4 | <0.0001 | 438.1 | 7495 | <0.0001 | 110.1 | 516 | <0.0001 | 645.8 | 19345 | <0.0001 |
| D7 | 45.16 | 100.8 | 0.0007 | 300.1 | 7461 | <0.0001 | 117.3 | 608.5 | <0.0001 | 541.7 | 15964 | <0.0001 |
| F3 | 49.51 | 65.58 | 0.3793 | 1149 | 2805 | 0.17 | 171.7 | 616.6 | <0.0001 | 1675 | 10606 | <0.0001 |
| F4 | 101.9 | 146 | 0.1435 | 3970 | 3043 | 0.6512 | 605.4 | 643.6 | 0.8019 | 16141 | 13886 | 0.822 |
| F9 | 37.37 | 80.12 | 0.0069 | 737.6 | 5780 | <0.0001 | 134.9 | 478.8 | <0.0001 | 1325 | 28234 | <0.0001 |
| H3 | 45.09 | 118.8 | 0.0006 | 337.4 | 10441 | <0.0001 | 105.2 | 539.6 | <0.0001 | 688.1 | 20531 | <0.0001 |
| 5/8Hyb | 21.44 | 115.2 | <0.0001 | 1214 | 5902 | 0.0013 | 142.5 | 512.6 | <0.0001 | 2071 | 18231 | <0.0001 | x = could not calculate;
>max = calculated value greater than the maximum concentration used Antiviral Activity of the Selected Hybrid IFNs The 13 selected hybrid IFNs were arrayed on plates in triplicate and over a broader range of dilutions than used in the down-selection screenings. For these studies IFN-α2a-His was used for comparison because it appeared to be more stable than IFN-alfacon when arrayed on the plates. To control for the possibility that the antiviral activity measured was related to reduction in cell proliferation rather than to a direct effect on the virus, cell inhibition assays were performed in Daudi cells, an Epstein-Barr virus-transformed human B-cell line that is highly sensitive to IFN-α (Nederman et al., 1990). None of the hybrid IFNs showed significantly greater antiproliferative activity for cells than did the IFN-α2a control when both $IC_{50}$ and $IC_{90}$ values were compared (Table 3). In contrast, statistical analysis of the antiviral inhibition assays revealed that almost all of the hybrid IFNs demonstrated significantly enhanced antiviral activity against RVFV and VEEV as compared to the plant-derived IFN-α2a-His control in a same-plate direct comparison (Table 2). Similar statistical analysis was not possible for EBOV and MPXV because of the poor activity of the control IFN-α2a against these viruses in the assay. Nevertheless, it was observed that many of the hybrid IFNs did inhibit viral replication, especially for EBOV, as indicated by both leftward and downward shifts in their dose-response curves. For example, dose response curves of hybrid IFNs IFN-B4 and -H3 illustrate their antiviral activity against each of the four viruses tested (FIG. 4).

TABLE 3

Comparison of the inhibitory characteristics of the shuffled IFNs by Daudi cell inhibition assay.

| | IC50 (pg/ml) | | | IC90 (pg/ml) | | |
|---|---|---|---|---|---|---|
| IFN | Drug | IFN- | P-value | Drug | IFN-α2a | P-value |
| A5 | 94.59 | 79.17 | 0.0365 | 163.9 | 179.2 | 0.6848 |
| B | 58.78 | 62.36 | 0.5415 | 217.1 | 228.3 | 0.7844 |
| B | 59.79 | 57.41 | 0.6298 | 186.3 | 229.4 | 0.2021 |
| B | 54.86 | 58.64 | 0.5081 | 239.3 | 266.8 | 0.5634 |
| B | 52.03 | 57.45 | 0.3694 | 201.8 | 211.6 | 0.8211 |
| D3 | 54.26 | 53.82 | 0.9198 | 190.7 | 230.8 | 0.2231 |
| D5 | 79.77 | 58.27 | 0.0048 | 315.4 | 280.8 | 0.5724 |
| D7 | 73.7 | 57.74 | 0.0223 | 322.4 | 275.9 | 0.4322 |
| F3 | 55.89 | 57.13 | 0.8214 | 193.2 | 238.7 | 0.2569 |
| F4 | 70.07 | 58.87 | 0.082 | 267.1 | 269.6 | 0.9625 |
| F9 | 61.05 | 38.5 | 0.0353 | 271.9 | 304.1 | 0.7526 |
| H3 | 79.61 | 44.15 | <0.0001 | 383.9 | 253 | 0.0838 |
| 5/8 Hyb | 51.65 | 61.08 | 0.14 | 169.4 | 264.5 | 0.0414 |

Sequence Comparison of the Hybrid IFNs

To gain insight into properties of the hybrid IFN that could have contributed to improved antiviral activities, their nucleotide sequences were determined then aligned and compared their derived amino acid sequences to those of controls. In particular, changes in key amino acids known to be important for binding to the IFN receptors IFNAR-1 and IFNAR-2 (FIG. 5, boxed regions) (Kumaran et al., 2007; Pan et al., 2008; Roisman et al., 2005; Uze et al., 2007) were of interest. In general, IFN binds initially to IFNAR-2 with a high affinity followed by a much lower affinity binding to IFNAR-1, initiating a signaling cascade [reviewed in (Uze et al., 2007)]. Because changes in these key amino acids could differentially regulate downstream signaling cascades, subtle amino acid changes might dramatically change biological activities. Comparing amino acids implicated in IFNAR-2 binding (FIG. 5, numbered with respect to IFN-alphacon-1) revealed that 10 of 13 critical amino acids (A19, F27, L30, R33, D35, R145, A146, M149, R150, and S153) were conserved among all of the hybrid IFNs and were the same as those found in both IFN-α2a and alfacon-1. Two of the remaining three amino acids implicated in IFNAR-2 binding (positions 16 and 26), were shared among most of the hybrid IFNs, alfacon-1, and most of the parents except for IFN-α2a. The final known amino acid that relates to IFNAR-2 binding, (L154 for both alfacon-1 and IFN-α2a) was changed to F154 in five of the hybrid IFNs. This F154 was also seen in IFN-α4, IFN-α10, IFN-ε and IFN-β1 (FIG. 5).

Similar findings were observed with respect to residues reported to be important for IFNAR-1 binding, in that 8 of 11 key amino acids (E59, Q62, F65, N66, T70, L81, Y86, L118)

were the same in IFN-α2a, alfacon-1, and all of the hybrid IFNs. The most consistent change in the hybrid IFNs with respect to IFNAR-1 binding residues, was at position 90, where 11 of the 13 hybrid IFNs had D90 instead of the Y90 that is found in both IFN alfacon-1 and IFN-α2a. This D90 residue was also seen in FN-α8 but not in other IFN parents and could potentially be important in that IFN-α8 has the most potent antiviral activity of the natural IFN-α subtypes and binds with high affinity to IFNAR (Foster et al., 1996). For one of the remaining two known important IFNAR-1 binding residues (position 121), all but one of the hybrid IFNs had R121 like IFN-α2a. The one exception (IFN-D7), instead had K121 like IFN alfacon-1. At the final site, (position 58), one hybrid IFN (IFN-F9) differed from IFN-α2a, alfacon-1 and all of the other hybrid IFNs with a change from H58 to Y58 which part of an 8 amino acid insertion derived from IFN-β (FIG. 5). In mutagenesis studies by others, changing this H58 to A58 resulted in stronger binding to IFNAR-1 (Roisman et al., 2005). Similarly, the loss of the positively charged H58 in IFN-F9 could result in stronger IFNAR-1 binding and contribute to the observed more potent antiviral properties. To confirm the biological significance of any of the changes, further mutagenesis and binding studies may be required.

In addition to the noted potential amino acid changes in the hybrid IFNs that could influence IFNAR binding, other consistent amino acid changes were observed among the hybrid IFNs. For example, Y113 was seen in all but two (F9, D7) of the hybrid IFNs as well as in IFN-α8 but not in any of the other parental IFNs or in IFN-alfacon-1. Similarly, E37, E84, I87, S109 and S138 were found in more than half of the hybrid IFNs and in IFN-α8 but not in any of the other IFN-α parents (FIG. 5). Other differences with both IFN-α2a and IFN-alfacon-1 that were conserved in the majority of the hybrid IFN were M102 and K160. These residues were also found in IFN-α8 and two other parental IFN-α subtypes (FIG. 5).

Analysis of the Selection Pressure for Individual Amino Acids in the Hybrid IFNs To obtain a more objective view of the bias toward the appearance of particular amino acids at each position in the selected hybrid IFNs, an in silico analytic comparison of the frequency of occurrence of individual amino acids at specified positions between the set of 13 high potency IFNs and a representative set of all the hybrid IFNs produced was performed. This approach allowed the detection of a "selection pressure" at particular residue sites that could potentially result in enhanced antiviral activity. For this, a multiple sequence alignment was generated by using an initial set of 431 hybrid IFN sequences (INIT-431) representing a good cross section of the overall parental sequence distributions in the IFN-α/IFN-α hybrid library. Next, a second multiple sequence alignment using the amino acid sequences of the 13 high-activity hybrid IFNs (FINAL-13) was produced. Each residue-position in the alignments was assessed and the frequency of occurrence of each amino acid was computed. Examples of positions in the amino acid sequence of the IFNs showing substantial shifts in the residue preference (Δf) between sets INIT-431 and FINAL-13 is presented in FIG. 6, and a more extensive list is provided in Table 4. In some cases, 100% of the final hybrid IFNs that were selected had an amino acid at a certain position that was not the most prevalent one at that position in early rounds of GRAMMR (e.g. FIG. 6, position 86). Clear biases were observed both toward selection of specific residues not known to relate to IFNAR binding (e.g., FIG. 6B, position 37) as well as toward selection of residues that have been implicated in receptor binding (e.g. FIG. 6, position 16 for IFNAR-2 and position 90 for IFNAR-1).

Amino acid sequences of the selected hybrid IFNs include the following:

>10491-A5
(SEQ ID NO: 02)
CDLPQTHSLGNRRALILLAQMGRISLFSCLKDRHDFEFPQEEFGHQFQ

KAETIPVLHEMIQQIFNLFSTKDSSAAWDETLLDEFYIELDQQLNDLE

ACMMQEVGVIESPLMYEDSILAVRKYFQRITLYLTEKKYSSCAWEVVR

AEIMRSLSFSTNLQKRLRRKE

>10491-B3
(SEQ ID NO: 03)
CDLPQTHSLGNRRALILLAQMRRISPFSCLKDRHDFEFPQEEFDDKQF

QKAQAISVLHEMIQQTFNLFSTKDSSAALDETLLDEFYIELDQQLNDL

EACMMQEVGVIESPLMYEDSILAVRKYFQRITLYLTEKKYSSCAWEVV

RAEIMRSFSLSINLQKRLRRKEL

>10491-B4
(SEQ ID NO: 04)
CDLPQTHSLGSRRTLMLLAQMRKISLFSCLKDRHDFEFPEEEFGNQFQ

KAETIPVLHEMIQQIFNLFSTEDSSAAWDETLLEKFYIELDQQLNDLE

ACVIQGVGVEESPLMYEDSILAVRKYFQRITLYLTEKKYSSCAWEVVR

AEIMRSFSLSINLQKRLRSKE

>10491-B5
(SEQ ID NO: 05)
CDLPQTHSLGNRRALILLAQMRRISPFSCLKDRHDFEFPQEEFDDHQF

QKAQAISVLHEMIQQTFNLFSTKDSSAAWDETLLDEFYIELDQQLNDL

EACMMQEERVIESPLMYEDSILAVRKYFRRITLYLTEKKYSSCAWEVV

RAEIMRSFSLSINLQKRLKSKE

>10491-B9
(SEQ ID NO: 06)
CDLPQTHSLGNRRALILLAQMRRISPFSCLKDRHDFEFPQEEFDDKQF

QKAQAISVLHEMIQQTFNLFSTKDSSAALDETLLDEFYIELDQQLNDL

EACMMQEVGVIESPLMYEDSILAVRKYFQRITLYLTEKKYSSCAWEVV

RAEIMRSFSLSTNLQKRLRSKE

>10491-D3
(SEQ ID NO: 07)
CDLPQTHSLGNRRALILLAQMGRISPFSCLKDRHDFEFPQEEFDGHQF

QKAQAISVLHEMIQQTFNLFSTKDSSAAWDETLLDEFYIELDQQLNDL

EACMMQEVGVIESPLMYEDSILAVRKYFQRITLYLTEKKYSSCAWEVV

RAEIMRSLSFSTNLQKRLRRKE

>10491-D5
(SEQ ID NO: 08)
CDLPQTHSLGNRRALILLAQMGRISPFSCLKDRHDFEFPEEEFDGHQF

QKAQAISVLHEMIQQTFNLFSTEDSSAALDETLLEKFYIELDQQLNDL

EACVIQEVGVEESPLMYEDSILAVRKYFQRITLYLTEKKYSSCAWEVV

RAEIMRSLSFSTNLQKRLRRKE

-continued

```
>10491-D7
                                        (SEQ ID NO: 09)
CDLPQTHSLGNRRALILLAQMRRISPFSCLKDRHDFEFPQEEFDDKQF
QKAQAISVLHEMIQQTFNLFSTKDSSAALDETLLDEFYIELDQQLNDL
EACVMQEERVGETPLMNADSILAVKKYFRRITLYLTEKKYSPCAWEVV
RAEIMRSFSLSINLQKRLKSKE
```

```
>10491-F3
                                        (SEQ ID NO: 10)
CDLPQTHSLGNRRALILLAQMRRISPFSCLKDRHDFEFPQEEFDGHQF
QKAQAISVLHEMIQQTFNLFSTKDSSAAWEQTLLDEFYIELDQQLNDL
EACMMQEVGVEESPLMYEDSILAVRKYFQRITLYLTEKKYSSCAWEVV
RAEIMRSLSFSTNLQKRLKSKE
```

```
>10491-F4
                                        (SEQ ID NO: 11)
CDLPQTHSLGSRRTLMLLAQMRRISLFSCLKDRHDFGFPQEEFGNQFQ
KAETIPVLHEMIQQIFNLFSTKDSSAAWDETLLDKFYTELYQQLNDLE

ACVIQGVGVTETPLMYEDSILAVRKYFQRITLYLKEKKYSPCAWEVVR

AEIMRSFSLSTNLQESLRSKE
```

-continued

```
>10491-F9
                                        (SEQ ID NO: 12)
CDLPQTHSLGSRRTLMLLAQMRKISLFSCLKDRHDFGFPQEEFGNQFQ
KEDAALTIYEMIQQIFNLFSTKDSSAAWDETLLDKFYTELYQQLNDLE
ACVIQGVGVTETPLMKEDSILAVRKYFQRITLYLKEKKYSPCAWEVVR
AEIMRSFSLSTNLQESLRSKE
```

```
>10491-H3
                                        (SEQ ID NO: 13)
CDLPQTHSLGNRRALILLAQMGRISPFSCLKDRHDFEFPQEEFDGHQF
QKAQAISVLHEMIQQTFNLFSTEDSSAAWDETLLEKFYIELDQQLNDL
EACVIQEERVGESPLMYEDSILAVRKYFRRITLYLTEKKYSSCAWEVV
RAEIMRSLSFSTNLQKRLRRKE
```

```
>08617_F10 (5/8Hyb)
                                        (SEQ ID NO: 14)
CDLPQTHSLGNRRALILLAQMRRISPFSCLKDRHDFEFPQEEFDDKQF
QKAQAISVLHEMIQQTFNLFSTKDSSAALDETLLDEFYIELDQQLNDL
EACMMQEVGVIESPLMYEDSILAVRKYFQRITLYLTEKKYSSCAWEVV
RAEIMRSFSL SINLQKRLKSKE
```

TABLE 4

Amino acid preference at selected positions among the final 13 hybrid IFNs.

| Alignment position | Pool of 431 shuffled sequences | | Final set of 13 sequences Frequency (%) | Frequency change (Δf) | Reference aa in alphacon-1 |
|---|---|---|---|---|---|
| | Residue type | Frequency (%) | | | |
| 14 | T | 46.2 | 23.1 | -23.1 | A14 |
| | A | 53.8 | 76.9 | 23.1 | |
| | | | | 0.0 | |
| 16 | V | 10.7 | 0.0 | -10.7 | I16 |
| | M | 51.3 | 23.1 | -28.2 | |
| | I | 38.1 | 76.9 | 38.8 | |
| 22 | R | 32.3 | 69.2 | 36.9 | R22 |
| | G | 55.0 | 30.8 | -24.2 | |
| | S | 12.8 | 0.0 | -12.8 | |
| 31 | K | 83.5 | 100.0 | 16.5 | K31 |
| | M | 16.5 | 0.0 | -16.5 | |
| 37 | R | 5.8 | 0.0 | -5.8 | G37 |
| | G | 83.1 | 15.4 | -67.7 | |
| | E | 11.1 | 84.6 | 73.5 | |
| 46 | N | 61.9 | 23.1 | -38.8 | N46 |
| | S | 3.5 | 0.0 | -3.5 | |
| | H | 26.0 | 46.2 | 20.2 | |
| | K | 8.6 | 30.7 | 22.1 | |
| 77 | W | 89.3 | 61.5 | -27.8 | W77 |
| | L | 10.7 | 38.5 | 27.8 | |
| 83 | D | 58.2 | 76.9 | 18.7 | E83 |
| | E | 41.8 | 23.1 | -18.7 | |
| 84 | Q | 6.5 | 0.0 | -6.5 | K84 |

TABLE 4-continued

Amino acid preference at selected positions among the final 13 hybrid IFNs.

|     |   |      |       |       |      |
|-----|---|------|-------|-------|------|
|     | K | 83.8 | 38.5  | -45.3 |      |
|     | E | 9.7  | 61.5  | 51.8  |      |
| 86  | H | 7.4  | 0.0   | -7.4  | Y86  |
|     | Y | 35.5 | 100.0 | 64.5  |      |
|     | S | 41.3 | 0.0   | -41.3 |      |
|     | C | 15.8 | 0.0   | -15.8 |      |
| 87  | T | 90.7 | 15.4  | -75.3 | T87  |
|     | I | 9.3  | 84.6  | 75.3  |      |
| 90  | H | 6.5  | 0.0   | -6.5  | Y90  |
|     | Y | 65.7 | 15.4  | -50.3 |      |
|     | D | 12.1 | 84.6  | 72.5  |      |
|     | N | 15.8 | 0.0   | -15.8 |      |
| 100 | L | 9.7  | 0.0   | -9.7  | V100 |
|     | V | 75.6 | 45.5  | -30.1 |      |
|     | M | 14.6 | 54.5  | 39.9  |      |
| 101 | L | 9.7  | 0.0   | -9.7  | I101 |
|     | I | 58.7 | 46.2  | -12.5 |      |
|     | M | 31.6 | 53.8  | 22.3  |      |
| 107 | G | 20.9 | 15.4  | -5.5  | E107 |
|     | T | 12.3 | 15.4  | 3.1   |      |
|     | A | 0.2  | 0.0   | -0.2  |      |
|     | E | 57.5 | 23.1  | -34.4 |      |
|     | I | 8.4  | 46.2  | 37.8  |      |
|     | D | 0.5  | 0.0   | -0.5  |      |
|     | V | 0.2  | 0.0   | -0.2  |      |
| 109 | S | 20.0 | 76.9  | 56.9  | T109 |
|     | T | 80.0 | 23.1  | -56.9 |      |
| 113 | I | 9.7  | 0.0   | -9.7  | N113 |
|     | K | 14.6 | 7.7   | -6.9  |      |
|     | N | 64.7 | 7.7   | -57.0 |      |
|     | Y | 10.9 | 84.6  | 73.7  |      |
| 138 | D | 8.1  | 0.0   | -8.1  | P138 |
|     | P | 80.5 | 23.1  | -57.4 |      |
|     | S | 11.1 | 76.9  | 65.8  |      |
|     | R | 0.2  | 0.0   | -0.2  |      |
| 152 | L | 58.5 | 38.5  | -20.0 | F152 |
|     | F | 41.5 | 61.5  | 20.0  |      |
| 153 | F | 14.2 | 0.0   | -14.2 | S153 |
|     | S | 85.6 | 100.0 | 14.4  |      |
|     | C | 0.2  | 0.0   | -0.2  |      |
| 154 | L | 72.9 | 61.5  | -11.4 | L154 |
|     | F | 27.1 | 38.5  | 11.4  |      |
| 156 | T | 63.3 | 61.5  | -1.8  | T156 |
|     | I | 8.8  | 38.5  | 29.7  |      |
|     | A | 15.5 | 0.0   | -15.5 |      |
|     | K | 12.3 | 0.0   | -12.3 |      |
| 160 | E | 69.4 | 15.4  | -54.0 | E160 |
|     | K | 30.6 | 84.6  | 54.0  |      |
| 163 | R | 86.8 | 69.2  | -17.6 | R163 |
|     | K | 13.2 | 30.8  | 17.6  |      |
| 164 | S | 38.7 | 61.5  | 22.8  | R164 |
|     | R | 61.3 | 38.5  | -22.8 |      |

■ ABS(Δf) > 50%

▓ 30% < ABS(Δf) < 50%

░ 20% < ABS(Δf) < 30%

Structural Modeling of Amino Acid Changes in the Hybrid IFNs

Studies by others suggest that potent IFNs have more highly positively-charged C-terminal tail residues, which can interact with a negatively charged region of IFNAR-2 (Slutzki et al., 2006). The instant hybrid IFNs conform to this trend with five of the hybrid IFNs, IFN-A5, -B3, -D3, -D5, -H3, sharing a tail with a net charge of +4 not found in any of the parents (KRLRRKE (SEQ ID NO: 15)). Six other hybrid IFNs have one of two tails with a net charge +3 and these can be divided in two subsets: (i) IFN-5/8 Hyb, -B5, -D7, and -F3, which derived their tails from IFN-α8 (KRLKSKE (SEQ ID NO: 16)); and (ii) B4 and B9 with tails not found in the parents (KRLRSKE (SEQ ID NO: 17)). The remaining two hybrid IFNs, IFN-F9 and -F4, derived their tails with a net charge of 0 from IFN-α2a (ESLRSKE (SEQ ID NO: 18)). To visualize how the residues in these charged tails might impact IFNAR binding, structural models based on a recently solved experimental structure of IFN-α2 in complex with IFNAR-2 (Nudelman, #5) (PDB code: 2KZ1) were generated. Examination of the 3D model generated for one of the hybrid IFNs with the +4 tail, IFN-H3, revealed that three residue-residue interactions involving salt bridge formation are likely to occur: IFN-H3 residues R163, R164 and K165 interacting with IFNAR-2 residues D70, E134 and E133, respectively (FIG. 7C, D).

Based on the models, it is also likely that the selection of positive residues in the hybrid IFNs at positions 160 and 161 relates to changes in receptor binding. In the NMR experimental structure, position E160 of IFN-α2 appears to have a mobile side chain that switches H-bond partners from IFN-α2 S11 and T156, to IFN-α2 R12 and/or IFNAR-2 H76. The replacement of E160 with the positively-charged K160 residue in most of the hybrid IFNs (e.g. IFN-H3, FIG. 7) would have a marked effect on the dynamics of the neighboring residues. In addition to the expected effect on the H-bonding partners mentioned above, it is likely that the ionization state of residues such as IFNAR-2 H76 and H187 would be substantially altered; thus, impacting the interaction between the IFN and the receptor. Also, R161, which is present in all of the charged tails of the hybrid IFNs, is predicted to interact with one or two negatively-charged residues within that the same IFN molecule: a D residue common at position 44 (as in IFN-B3, -B5, -B9, -D3, -D5, -D7, -F3 and -5/8 Hyb); and/or an E residue at position 40 (as in IFN-B4, and -B5). In contrast, when position 161 is occupied by S (as in IFN-α2a and the hybrid IFNs with a 0 charge tail), none of these negative residues are present in that same IFN molecule, with position 44 corresponding to a deletion and position 40 occupied by a Q residue, so the S161 side-chain is expected to interact instead with N157 (in IFN) and Q136 in IFNAR-2 as shown in the published model (Nudelman et al., 2010). Although one may not be able to accurately predict how such changes influence the interactions of the tail region of the IFN with IFNAR, it is logical to presume that they have some impact on the dynamics of binding.

The structural models were also used to attempt to correlate differences in antiviral activities among the hybrid IFNs. For this, the predicted amino acid sequences of the hybrid IFNs were first aligned to determine the minimum number of parents required to produce each hybrid sequence. By mapping the residue differences between parents into the structural models a few potential interactions were identified that could have contributed to increased antiviral activity, some of which provide support for the importance of interaction between more positively charged tails and IFNAR-2. For example, IFN-B3 differs by only two residues from IFN-5/8 Hyb, so the higher $IC_{50}$ and $IC_{90}$ values measured for the IFN-B3 molecule (Table 2) may likely be due to the two R residues at the C-terminal end of the molecule that were inherited from IFN-α4 (FIG. 8A). The structural model of IFN-B3 predicts that both of these residues interact directly with IFNAR-2, which probably leads to increased binding (FIG. 8B). An equivalent analysis for IFN-B9 leads to a similar conclusion (FIG. 8C).

In contrast, the increased antiviral activity of some of the IFN cannot be attributed to IFN-IFNAR-2 interactions. For example, IFN-F9 represents a modification of IFN-α2a in which a fragment (residues 51-58, Table 5) was inherited from IFN-β. When the sequence is mapped into a 3D model the altered fragment is seen as part of an α-helix that lies on the opposite side of the expected surface of interaction of the IFN with IFNAR-2 (FIG. 8D). A similar case is observed for IFN-D7 (FIG. 8E). The increased antiviral properties of these IFN cannot be explained by a direct alteration of the known IFN-IFNAR-2 interaction surface. It is possible that the observed changes impact interactions with IFNAR-1, but at present there is no experimental structure to corroborate this hypothesis. Similar analyses of the remaining hybrid IFN sequences show that residue-optimization tended to occur in different regions on the IFN molecules, distant from the experimentally-observed IFN-IFNAR-2 interaction surface (e.g., IFN-F4, FIG. 8F).

Discussion

The study reported herein had two major goals: (1) to derive synthetic human IFNs with better antiviral activities than parental natural IFNs against a broad range of biodefense-related viruses; and, (2) to gain a basic understanding of the factors that contributed to improved IFN potency. In addition to these major goals, it was also of interest to evaluate plant expression as a rapid, cost-effective and scalable manufacturing system for downstream applications. Toward these goals, hybrid type 1 human IFN genes were generated, and those genes were transiently expressed in *Nicotiana benthamiana* plants. Further, the IFNs were screened against four very diverse highly pathogenic viruses, and used in silico modeling tools to define characteristics of the IFNs that could have led to increased, broad spectrum activity.

The novel IFNs were created by intermixing genes from seven IFN-α subtypes, as well as those of IFN-β1, -ε, -κ and -ω using a process termed GRAMMR™. In contrast to PCR-based gene shuffling methods, GRAMMR™ can be used to quickly hybridize sizeable and fairly diverse genes with few dysfunctional genes produced. During the process, DNA heteroduplexes are formed by the annealing of complementary strands of various parent plasmids. In areas where non-complementary nucleotides are located, a mismatch endonuclease is used to cleave one strand at the mismatch and then a proofreading polymerase is used to replace nucleotides using the opposite strand as template. Finally the plasmid is resealed with DNA ligase. GRAMMR™ favors recovery of the hybrid genes over re-annealed homologous parent strands because the homoduplex DNAs remains linear whereas the heteroduplex DNAs are able to circularize due to the staggered termini created during linearization and because circular DNA can transform bacteria more efficiently than linear DNA.

For practical use, especially for biodefense purposes, therapeutic proteins such as IFNs may need to be produced cheaply, safely, and in high yields. All of these issues can be addressed by the use of plants as the expression system. In this study, the hybrid IFN genes were constructed in a TMV-based plasmid vector and then in vitro-transcribed RNAs were introduced from these vectors into *Nicotiana benthamiana* plants to initiate TMV RNA replication and high yield production of the encoded IFNs. A similar system was used to produce therapeutic proteins that have already been tested and shown safe in clinical studies in humans (McCormick and Palmer, 2008) and more recently, to generate large quantities of an entry inhibitor to prevent HIV-1 infections (O'Keefe et al., 2009). Although the instant expression work involved only small scale production of the IFNs, in our experience, the system used can produce more than 1 g of recombinant protein per kilogram of plant tissue. In addition to scale-up possibilities, plants can possess enzymes such as foldases, which can facilitate proper conformations of mammalian-derived proteins, and they may not have harmful proteins such as endotoxins, which occur in bacteria. Plants also do not have the oncogenic viruses sometimes found in mammalian cells, which provides a measure of safety for human applications of the expression products. Finally, because it is possible to inoculate hundreds of plants in parallel, this system can be an excellent means for producing laboratory quantities of multiple proteins for screening studies.

To address the identification of IFNs with enhanced broad-spectrum potency, the antiviral activities of more than 1400 plant-derived hybrid IFNs were compared against three RNA viruses and one DNA virus from four different families: Filoviridae (EBOV), Bunyaviridae (RVFV), Togaviridae (VEEV) and Poxviridae (MPXV). Evolutionary pressures applied in the development process included both primary selection for high expression levels in plants and secondary selection for strong antiviral activity against four extremely different, highly pathogenic viruses with varying sensitivities to type 1 IFN. In particular, the DNA virus, MPXV, was not expected to be as susceptible to the antiviral properties of the type 1 IFN as the RNA viruses, yet improved activity against MPXV with numerous hybrid IFNs was seen. The final set showed enhanced activity against all of the viruses in vitro as compared to IFN-α2a. While extensive same-plate comparisons of the final set of 13 hybrid IFNs to pharmaceutical grade IFN-alfacon-1 (Infergen) were not performed in this study, they were compared in early screenings both to Infergen and to plant-derived IFN-alfacon-His, the latter of which was modified to have codons optimized for plant expression, a KDEL (SEQ ID NO: 31) sequence for compartmentalization, and a His-tag for purification. Two notable findings came from those studies. First, numerous hybrid IFNs were detected that performed as well as or better than both consensus IFNs against one or more of the viruses. Second, it was found that the plant-derived IFN-alfacon-His was as effective against the viruses that were tested as Infergen; thus, in addition to producing novel IFNs, the plant expression system used could offer a convenient and cost-effective means to manufacture large quantities of IFN-alfacon.

To gain an understanding of factors that might have contributed to the potency of the hybrid IFNs, their nucleotide sequences were compared to those of the parents. Numerous consistently selected and highly preferred amino acids were noted at cognate locations of the hybrid IFNs. Interestingly, many of these amino acid changes are also present in IFN alfacon-1, which is more potent than the natural type 1 IFNs. The increased potency of IFN-alfacon-1 has been attributed to a greater receptor binding affinity (Blatt et al., 1996; Klein et al., 1996), engagement of increased numbers of both high and low affinity receptors (Klein et al., 1996), and increased expression of certain IFN response genes (Klein et al., 1993). Some of the changes noted may relate to the enhanced potency of IFN-alfacon-1 as well as the hybrid IFNs. In particular, it is likely that amino acid changes that influence receptor binding affinities can influence the complex biological processes initiated by that binding. Although it was not possible to assign significance to many of the amino acids that appeared in the hybrid IFNs some changes were noted that may be involved in improved potency due to their influence on IFNAR binding. For example, addition of positively charged amino acids to regions of the hybrid IFN predicted to bind to IFNAR would be expected to increase binding to the positively charged areas of the receptor. The replacement of the negative and neutral amino acids at positions E160 and S161 in IFN-α2a with the positive residues K160 and R161 in most of the hybrid IFN fit this criterion. To our knowledge, these residues have not been previously identified as important for IFNAR-2 binding; however, earlier data supporting the enhanced potency of negatively charged C-terminal tail regions came from studies by Slutzki and colleagues who showed that replacing the C-terminal tail of IFN-α2 with the more positively charged tail of IFN-α8, which included the same K160 and R161 residues as seen in the hybrid IFNs, enhanced IFN-α2's antiviral properties by increasing the IFN's affinity for IFNAR-2 (Slutzki et al., 2006).

Additional amino acid changes in the hybrid IFNs were also predicted to impact binding to IFNAR-2 as deduced from their proximity to the binding faces of the proteins when they were mapped to a recently solved experimental structure of IFN-α2 complexed with IFNAR-2, but others were located quite far from the interacting surfaces of the proteins. Consequently, some of these might be involved in binding to IFNAR-1, but at present there is no structural model of IFN and IFNAR-1 available for modeling potential interactions. One finding with the hybrid IFN that may be related to IFNAR-1 binding is the short segment of IFN-β that was identified in IFN-F9 (amino acids 51-58, FIG. 5). Part of this same region was previously implicated in improved antiviral activity of a PCR-generated, gene-shuffled IFN, and the improvement was thought to be due to higher affinity for IFNAR-1 (Brideau-Andersen et al., 2007). In particular, the change from H58 to Y58 seen in both the gene shuffled IFN and IFN-F9 appears to be significant in that occurred both in IFN-F9 and in the previously published recombinant IFN, and because in alanine scanning mutagenesis studies, changing it to A58 resulted in increased IFNAR-1 binding (Roisman et al., 2005).

In summary, this study demonstrates that it is possible to generate novel IFN with enhanced in vitro activity against multiple highly pathogenic viruses and that the improvement is due at least in part to changes that are expected to influence receptor binding. The instant work also indicates that plant-derived IFNs can be as potent in such assays as the homologous, commercially available bacterial-IFN. Additional studies to validate these findings in animal models can be performed. Because these are human IFNs, ultimately this will require clinical assessment; however, studies with IFN-alfacon-1 in hamsters showed it to be effective against West Nile, Pichinde, or Punta Toro viruses, demonstrating that human IFN can be evaluated in a small animal model (Gowen et al., 2005; Gowen et al., 2008; Morrey et al., 2004a; Morrey et al., 2004b). The hybrid IFNs can be similarly assessed to determine if the instant in vitro findings can be correlated with in vivo prophylaxis of therapy.

It should be understood, of course, that the foregoing relates to exemplary embodiments of the invention and that modifications may be made without departing from the spirit and scope of the invention as set forth in the following claims.

REFERENCE LISTING

Basler, C. F., Wang, X., Muhlberger, E., Volchkov, V., Paragas, J., Klenk, H. D., Garcia-Sastre, A., Palese, P., 2000. The Ebola virus VP35 protein functions as a type I IFN antagonist. Proc Natl Acad Sci USA 97, 12289-12294.

Berman, H. M., Westbrook, J., Feng, Z., Gilliland, G., Bhat, T. N., Weissig, H., Shindyalov, I. N., Bourne, P. E., 2000. The Protein Data Bank. Nucleic Acids Res 28, 235-242.

Billecocq, A., Spiegel, M., Vialat, P., Kohl, A., Weber, F., Bouloy, M., Haller, O., 2004. NSs protein of Rift Valley fever virus blocks interferon production by inhibiting host gene transcription. J Virol 78, 9798-9806.

Blatt, L. M., Davis, J. M., Klein, S. B., Taylor, M. W., 1996. The biologic activity and molecular characterization of a novel synthetic interferon-alpha species, consensus interferon. J Interferon Cytokine Res 16, 489-499.

Bouloy, M., Janzen, C., Vialat, P., Khun, H., Pavlovic, J., Huerre, M., Haller, O., 2001. Genetic evidence for an interferon-antagonistic function of rift valley fever virus nonstructural protein NSs. J Virol 75, 1371-1377.

Bray, M., 2001. The role of the Type I interferon response in the resistance of mice to filovirus infection. J Gen Virol 82, 1365-1373.

Brideau-Andersen, A. D., Huang, X., Sun, S. C., Chen, T. T., Stark, D., Sas, I. J., Zadik, L., Dawes, G. N., Guptill, D. R., McCord, R., Govindarajan, S., Roy, A., Yang, S., Gao, J., Chen, Y. H., Skartved, N. J., Pedersen, A. K., Lin, D., Locher, C. P., Rebbapragada, I., Jensen, A. D., Bass, S. H., Nissen, T. L., Viswanathan, S., Foster, G. R., Symons, J. A., Patten, P. A., 2007. Directed evolution of gene-shuffled IFN-alpha molecules with activity profiles tailored for treatment of chronic viral diseases. Proc Natl Acad Sci USA 104, 8269-8274.

Chang, C. C., Chen, T. T., Cox, B. W., Dawes, G. N., Stemmer, W. P., Punnonen, J., Patten, P. A., 1999. Evolution of a cytokine using DNA family shuffling. Nat Biotechnol 17, 793-797.

Desmyter, J., Melnick, J. L., Rawls, W. E., 1968. Defectiveness of interferon production and of rubella virus interference in a line of African green monkey kidney cells (Vero). J Virol 2, 955-961.

Falkner, F. G., Moss, B., 1988. *Escherichia coli* gpt gene provides dominant selection for vaccinia virus open reading frame expression vectors. J Virol 62, 1849-1854.

Feng, Z., Cerveny, M., Yan, Z., He, B., 2007. The VP35 protein of Ebola virus inhibits the antiviral effect mediated by double-stranded RNA-dependent protein kinase PKR. J Virol 81, 182-192.

Foster, G. R., Rodrigues, O., Ghouze, F., Schulte-Frohlinde, E., Testa, D., Liao, M. J., Stark, G. R., Leadbeater, L., Thomas, H. C., 1996. Different relative activities of human cell-derived interferon-alpha subtypes: IFN-alpha 8 has very high antiviral potency. J Interferon Cytokine Res 16, 1027-1033.

Fried, M. W., Shiffman, M. L., Reddy, K. R., Smith, C., Marinos, G., Goncales, F. L., Jr., Haussinger, D., Diago, M., Carosi, G., Dhumeaux, D., Craxi, A., Lin, A., Hoffman, J., Yu, J., 2002. Peginterferon alfa-2a plus ribavirin for chronic hepatitis C virus infection. N Engl J Med 347, 975-982.

Goff, A., Twenhafel, N., Garrison, A., Mucker, E., Lawler, J., Paragas, J., 2007. In vivo imaging of cidofovir treatment of cowpox virus infection. Virus Res 128, 88-98.

Gowen, B. B., Barnard, D. L., Smee, D. F., Wong, M. H., Pace, A. M., Jung, K. H., Winslow, S. G., Bailey, K. W., Blatt, L. M., Sidwell, R. W., 2005. Interferon alfacon-1 protects hamsters from lethal pichinde virus infection. Antimicrob Agents Chemother 49, 2378-2386.

Gowen, B. B., Wong, M. H., Jung, K. H., Blatt, L. M., Sidwell, R. W., 2008. Prophylactic and therapeutic intervention of Punta Toro virus (Phlebovirus, Bunyaviridae) infection in hamsters with interferon alfacon-1. Antiviral Res 77, 215-224.

Habjan, M., Pichlmair, A., Elliott, R. M., Overby, A. K., Glatter, T., Gstaiger, M., Superti-Furga, G., Unger, H., Weber, F., 2009. NSs protein of rift valley fever virus induces the specific degradation of the double-stranded RNA-dependent protein kinase. J Virol 83, 4365-4375.

Harcourt, B. H., Sanchez, A., Offermann, M. K., 1999. Ebola virus selectively inhibits responses to interferons, but not to interleukin-1 beta, in endothelial cells. J Virol 73, 3491-3496.

Ikegami, T., Narayanan, K., Won, S., Kamitani, W., Peters, C. J., Makino, S., 2009. Rift Valley fever virus NSs protein promotes post-transcriptional downregulation of protein kinase PKR and inhibits eIF2alpha phosphorylation. PLoS Pathog 5, e1000287.

Ikegami, T., Won, S., Peters, C. J., Makino, S., 2006. Rescue of infectious rift valley fever virus entirely from cDNA, analysis of virus lacking the NSs gene, and expression of a foreign gene. J Virol 80, 2933-2940.

Jahrling, P. B., Geisbert, T. W., Geisbert, J. B., Swearengen, J. R., Bray, M., Jaax, N. K., Huggins, J. W., LeDuc, J. W., Peters, C. J., 1999. Evaluation of immune globulin and recombinant interferon-alpha2b for treatment of experimental Ebola virus infections. J Infect Dis 179 Suppl 1, S224-234.

Klaus, W., Gsell, B., Labhardt, A. M., Wipf, B., Senn, H., 1997. The three-dimensional high resolution structure of human interferon alpha-2a determined by heteronuclear NMR spectroscopy in solution. J Mol Biol 274, 661-675.

Klein, S. B., Blatt, L. M., Taylor, M. W., 1993. Consensus interferon induces peak mRNA accumulation at lower concentrations than interferon-alpha 2a. J Interferon Res 13, 341-347.

Klein, S. B., Blatt, L. M., Taylor, M. W., 1996. Cell surface binding characteristics correlate with consensus type I interferon enhanced activity. J Interferon Cytokine Res 16, 1-6.

Kumaran, J., Wei, L., Kotra, L. P., Fish, E. N., 2007. A structural basis for interferon-alpha-receptor interactions. Faseb J 21, 3288-3296.

Lee, M. S., Bondugula, R., Desai, V., Zavaljevski, N., Yeh, I. C., Wallqvist, A., Reifman, J., 2009. PSPP: a protein structure prediction pipeline for computing clusters. PLoS One 4, e6254.

Lukaszewski, R. A., Brooks, T. J., 2000. Pegylated alpha interferon is an effective treatment for virulent venezuelan equine encephalitis virus and has profound effects on the host immune response to infection. J Virol 74, 5006-5015.

Mateo, M., Reid, S. P., Leung, L. W., Basler, C. F., Volchkov, V. E., 2010. Ebolavirus VP24 binding to karyopherins is required for inhibition of interferon signaling. J Virol 84, 1169-1175.

McCormick, A. A., Palmer, K. E., 2008. Genetically engineered Tobacco mosaic virus as nanoparticle vaccines. Expert Rev Vaccines 7, 33-41.

Morrey, J. D., Day, C. W., Julander, J. G., Blatt, L. M., Smee, D. F., Sidwell, R. W., 2004a. Effect of interferon-alpha and interferon-inducers on West Nile virus in mouse and hamster animal models. Antivir Chem Chemother 15, 101-109.

Morrey, J. D., Day, C. W., Julander, J. G., Olsen, A. L., Sidwell, R. W., Cheney, C. D., Blatt, L. M., 2004b. Modeling hamsters for evaluating West Nile virus therapies. Antiviral Res 63, 41-50.

Morrill, J. C., Jennings, G. B., Cosgriff, T. M., Gibbs, P. H., Peters, C. J., 1989. Prevention of Rift Valley fever in rhesus monkeys with interferon-alpha. Rev Infect Dis 11 Suppl 4, S815-825.

Mosca, J. D., Pitha, P. M., 1986. Transcriptional and posttranscriptional regulation of exogenous human beta interferon gene in simian cells defective in interferon synthesis. Mol Cell Biol 6, 2279-2283.

Nederman, T., Karlstrom, E., Sjodin, L., 1990. An in vitro bioassay for quantitation of human interferons by measurements of antiproliferative activity on a continuous human lymphoma cell line. Biologicals 18, 29-34.

Nudelman, I., Akabayov, S. R., Schnur, E., Biron, Z., Levy, R., Xu, Y., Yang, D., Anglister, J., 2010. Intermolecular interactions in a 44 kDa interferon-receptor complex detected by asymmetric reverse-protonation and two-dimensional NOESY. Biochemistry 49, 5117-5133.

O'Keefe, B. R., Vojdani, F., Buffa, V., Shattock, R. J., Montefiori, D. C., Bakke, J., Mirsalis, J., d'Andrea, A. L., Hume, S. D., Bratcher, B., Saucedo, C. J., McMahon, J. B., Pogue, G. P., Palmer, K. E., 2009. Scaleable manufacture of HIV-1 entry inhibitor griffithsin and validation of its safety and efficacy as a topical microbicide component. Proc Natl Acad Sci USA 106, 6099-6104.

Pan, M., Kalie, E., Scaglione, B. J., Raveche, E. S., Schreiber, G., Langer, J. A., 2008. Mutation of the IFNAR-1 receptor binding site of human IFN-alpha2 generates type I IFN competitive antagonists. Biochemistry 47, 12018-12027.

Petrey, D., Xiang, Z., Tang, C. L., Xie, L., Gimpelev, M., Mitros, T., Soto, C. S., Goldsmith-Fischman, S., Kernytsky, A., Schlessinger, A., Koh, I. Y., Alexov, E., Honig, B., 2003. Using multiple structure alignments, fast model building, and energetic analysis in fold recognition and homology modeling. Proteins 53 Suppl 6, 430-435.

Roisman, L. C., Jaitin, D. A., Baker, D. P., Schreiber, G., 2005. Mutational analysis of the IFNAR1 binding site on IFNalpha2 reveals the architecture of a weak ligand-receptor binding-site. J Mol Biol 353, 271-281.

Samuel, C. E., 2001. Antiviral actions of interferons. Clin Microbiol Rev 14, 778-809, table of contents.

Simmons, J. D., White, L. J., Morrison, T. E., Montgomery, S. A., Whitmore, A. C., Johnston, R. E., Heise, M. T., 2009. Venezuelan equine encephalitis virus disrupts STAT1 signaling by distinct mechanisms independent of host shutoff. J Virol 83, 10571-10581.

Slutzki, M., Jaitin, D. A., Yehezkel, T. B., Schreiber, G., 2006. Variations in the unstructured C-terminal tail of interferons contribute to differential receptor binding and biological activity. J Mol Biol 360, 1019-1030.

Towner, J. S., Paragas, J., Dover, J. E., Gupta, M., Goldsmith, C. S., Huggins, J. W., Nichol, S. T., 2005. Generation of eGFP expressing recombinant Zaire ebolavirus for analysis of early pathogenesis events and high-throughput antiviral drug screening. Virology 332, 20-27.

Uze, G., Schreiber, G., Piehler, J., Pellegrini, S., 2007. The receptor of the type I interferon family. Curr Top Microbiol Immunol 316, 71-95.

Yin, J., Gardner, C. L., Burke, C. W., Ryman, K. D., Klimstra, W. B., 2009. Similarities and differences in antagonism of neuron alpha/beta interferon responses by Venezuelan equine encephalitis and Sindbis alphaviruses. J Virol 83, 10036-10047.

What is claimed is:

1. An isolated polypeptide comprising an amino acid sequence selected from the group consisting of: SEQ ID NO: 02-08 and 10-14.

2. The isolated peptide of claim 1 where the amino acid sequence is SEQ ID NO: 02.

3. The isolated peptide of claim 1 where the amino acid sequence is SEQ ID NO: 03.

4. The isolated peptide of claim 1 where the amino acid sequence is SEQ ID NO: 04.

5. The isolated peptide of claim 1 where the amino acid sequence is SEQ ID NO: 05.

6. The isolated peptide of claim 1 where the amino acid sequence is SEQ ID NO: 06.

7. The isolated peptide of claim 1 where the amino acid sequence is SEQ ID NO: 07.

8. The isolated peptide of claim 1 where the amino acid sequence is SEQ ID NO: 08.

9. The isolated peptide of claim 1 where the amino acid sequence is SEQ ID NO: 10.

10. The isolated peptide of claim 1 where the amino acid sequence is SEQ ID NO: 11.

11. The isolated peptide of claim 1 where the amino acid sequence is SEQ ID NO: 12.

12. The isolated peptide of claim 1 where the amino acid sequence is SEQ ID NO: 13.

13. The isolated peptide of claim 1 where the amino acid sequence is SEQ ID NO: 14.

14. A recombinant interferon (IFN) derived from multiple rounds of genetic reassortment by mismatch resolution wherein the recombinant interferon has improved antiviral activity relative to IFN-α2a, and wherein the recombinant interferon has an amino acid sequence selected from the group consisting of SEQ ID NO: 02-08 and 10-14.

15. The recombinant interferon of claim 14 wherein the recombinant interferon was created by intermixing genes from seven IFN-α subtypes, IFN-β1, IFN-ε, IFN-κ and IFN-ω.

16. The recombinant interferon of claim 14 wherein the improved antiviral activity is against Venezuelan equine encephalitis virus, Rift Valley fever virus, Monkeypox virus, and Ebola virus.

* * * * *